(12) United States Patent
Halazy et al.

(10) Patent No.: US 7,259,162 B2
(45) Date of Patent: Aug. 21, 2007

(54) BENZAZOLE DERIVATIVES AND THEIR USE AS JNK MODULATORS

(75) Inventors: Serge Halazy, Vetraz-Monthoux (FR); Dennis Church, Commugny (CH); Montserrat Camps, Versoix (CH); Pascale Gaillard, St. Julien-en-Genevois (FR); Jean-Pierre Gotteland, Beaumont (FR)

(73) Assignee: Applied Research Systems Ars Holding N.V., Curacao (NL)

( * ) Notice: Subject to any disclaimer, the term of this patent is extended or adjusted under 35 U.S.C. 154(b) by 627 days.

(21) Appl. No.: 10/168,718

(22) PCT Filed: Dec. 20, 2000

(86) PCT No.: PCT/EP00/13006

§ 371 (c)(1),
(2), (4) Date: Oct. 21, 2002

(87) PCT Pub. No.: WO01/47920

PCT Pub. Date: Jul. 5, 2001

(65) Prior Publication Data

US 2003/0162794 A1     Aug. 28, 2003

(30) Foreign Application Priority Data

Dec. 24, 1999   (EP) .................. 99811207

(51) Int. Cl.
C07D 417/06 (2006.01)
A61K 31/506 (2006.01)

(52) U.S. Cl. .................. 514/235.8; 514/252.11; 514/252.14; 514/256; 514/274; 544/122; 544/295; 544/296; 544/310; 544/315; 544/333

(58) Field of Classification Search ........... 514/256, 514/235.8, 252.11, 274, 252.14; 548/100; 544/122, 295, 296, 310, 315, 333
See application file for complete search history.

(56) References Cited

U.S. PATENT DOCUMENTS 2,918,369 A   12/1959  Doorenbos et al.
4,064,136 A   12/1977  Loew et al.

FOREIGN PATENT DOCUMENTS

| DE | 1 963 542 | 6/1971 |
|---|---|---|
| DE | 26 17 345 A1 | 3/1979 |
| EP | 0 364 765 A2 | 4/1990 |
| JP | 11-80155 | 3/1999 |
| WO | WO98/49188 A1 | 11/1998 |
| WO | WO99/21859 A1 | 5/1999 |

OTHER PUBLICATIONS

Johnson et al., Mitogen activated protein kinase pathways mediated by ERK, JNK, and p38 protein kinases, Dec. 6, 2002, vol. 298, pp. 1911-1912.*

Sah et al., Translation Inhibitors Sensitize Prostate Cancer Cells to Apoptosis Induced by Tumor Necrosis Factor-related Apoptosis-inducing Ligand (TRAIL) by Activating c-Jun N-terminal Kinase, The Journal of Biological Chemistry, vol. 278, No. 23, pp. 20593-26002, Jun. 2003.*
Augustin et al, *J Prakt Chem GE* 324(1):3-11 (1982): Beilstein Registry Nos. 5589714, 5589715, 5589716, 5589718, 5589719, 5589720, 5589721, 5589722, 5589723, and 5601864, Beilstein Institut fuer Literatur der Organischen Chemie (Database Crossfire 'Online!).
Biehl et al, "LDA (lithium diisopropylamide) mediated reactions of 1-naphthalynes with lithiated acetonitriles and 1,4-dipolar nucleophilic anions", *Synthesis* 9:885-889 (1993).
Chabaka et al, "Facile Synthesis of 2-Furyl-, 2-Pyrrolyl-, 2-Imidasolyl- and Pyrrolo-Azoles from 2-Substituted methylazoles", *Polish J Chem* 68:1317-1325 (1994).
Deshmukh et al, "An Investigation of the Influence of Haloarenes and Hetarylacetonitriles on the Competition between Possible Aryne Arylation and Tandem Addition-Rearrangement Pathways", *Heterocycles* 34(6):1239-1249 (1992) (Database Chemical Abstracts 'Online!—CAS, AN117-233221).
Fanghaenel et al, *J Prakt Chem GE* 4:590-606 (1988): Beilstein Registry Nos. 6226072, 6220826, 6220828, 6235458 and 6131469, Beilstein Institut fuer Literatur der Organischen Chemie (Database Crossfire 'Online!).
Hassan et al, "Reactions of Benzimidazolyl-Acetonitrile and Methanethiol with Eelectron Deficient Compounds", *Chemical Abstracts* 126(6):583 (Abstract No. 74791a) (1997), *Chemical Abstracts* 126(1):1990F (Formula Index), and *Heterocycl Commun* 2(5):441-446 (1996).
Huang et al, "Synthesis, Reactions, and Tautomerism of Ketene N,S-Acetals with Benzothiazoline Ring", *Chemische Berichte* 123(3):541-547 (1990).
Hunger et al, "Benzimidazol-Derivate und verwandte Heterocyclean VI) Synthese von Phenyl—1-aminoalkyl-benzimidazolyl-(2)]-essigsäure-estern und -amiden", *Halvetica Chimica Acta* 43(6);1727-1733 (1960).

(Continued)

*Primary Examiner*—Deepak Rao
(74) *Attorney, Agent, or Firm*—Browdy & Neimark, PLLC

(57) ABSTRACT

The present invention is related to benzazole derivatives notably for use as pharmaceutically active compounds, as well as to pharmaceutical formulations containing such benzazole derivatives. Said benzazole derivatives are efficient modulators of the JNK pathway, they are in particular efficient and selective inhibitors of JNK2 and/or 3. The present invention is furthermore related to novel benzazole derivatives as well as to methods of their preparation.

(I)

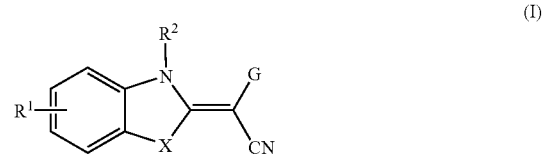

X is O, S or $NR^0$, with $R^0$ being H or an unsubstituted or substituted $C_1$-$C_6$ alkyl;

G is an unsubstituted or substituted pyrimidinyl group.

15 Claims, No Drawings

OTHER PUBLICATIONS

Kiprianov et al, *J Org Chem USSR* 1:757-762 (1965): Beilstein Registry Nos. 5395626, 5395012, 539500 and 5392953, Beilstein Institut fuer Literatur der Organischen Chemie (Database Crossfire 'Online!).

Kozynchenko et al, *Khim Geterotsikl Soedin RU* 8:1119-1123 (1988): Beilstein Registry Nos. 5115381, 5130108, 516287 and 5169755, Beilstein Institut fuer Literatur der Organischen Chemie (Database Crossfire 'Online!).

Kumage et al, "Human c-Jun N-terminal kinase expression and activiation in the nervous system", *Brain Res Mol Brain Res* 67(1):10-17 (1999).

Maroney et al, "Montoneuron apoptosis is blocked by CEP-1347 (KT 7515), a novel inhibitor of the JNK signaling pathway", *J Neurosci* 18(1):104-111 (1998).

Sabapathy et al, "JNK2 is required for efficient T-cell activation and apoptosis but not for normal lymphocyte development", *Curr Biol* 9(3):116-125 (1999).

Satzinger G, *Justus Liebigs Ann Chem*, pp. 473-511 (1978): Beilstein Registry No. 1128326, Beilstein Institut fuer Literatur der Organischen Chemie (Database Crossfire 'Online!).

Volovenko et al, "Syntehsis and biological activity of α-substituted 2-pyridylacetonitriles", *Chemical Abstracts* 117(23):850 (Abstract No. 233799a) (1992).

Xie et al, "Crystal structure of JNK3: a kinase implicated in neuronal apoptosis", *Structure* 6(8):983-991 (1998).

Yamanaka et al, *Heterocycles* 31(6):1115-1127 (1990): Beilstein Registry Nos. 3616487 and 3614951, Beilstein Institut fuer Literatur der Organischen Chemie (Database Crossfire 'Online!).

Yang et al, "Absence of excitotoxicity-induced apoptosis in the hippocampus of mice lacking the Jnk3 gene", *Nature* 389(6653):865-870 (1997).

Yang et al, "Differentiation of CD4+ T cells to Th1 cells requires MAP kinase JNK2", *Immunity* 9(4):575-585 (1998).

Zakhs et al, *J Org Chem USSR* 15:200 (1979): Beilstein Registry Nos. 855092, 861654 and 874268, Beilstein Institut fuer Literatur der Organischen Chemie (Database Crossfire 'Online!).

Database Accession No. 2001:22334—Chemical Abstracts Service and "Interbioscreen Compound Library" (Aug. 1, 2000) (Database Chemcats 'Online!).

Database Accession No. 2001:391108—Chemical Abstracts Service and "Enamine Product Listing" (Sep. 6, 2000) (Database Chemcats 'Online!).

Database Accession No. 2001:95296—Chemical Abstracts Service and "Enamine Product Listing" (Aug. 1, 2000) (Database Chemcats 'Online!).

* cited by examiner

BENZAZOLE DERIVATIVES AND THEIR USE AS JNK MODULATORS

This application is a 371 of PCT/EP00/13006 filed Dec. 20, 2000.

FIELD OF THE INVENTION

The present invention is related to benzazole derivatives and its tautomers for use as pharmaceutically active compounds, as well as pharmaceutical formulations containing such benzazole derivatives. In particular, the present invention is related to benzazole derivatives displaying a substantial modulatory, notably an inhibitory activity of the JNK (c-Jun-N-terminal Kinase) pathway and which are therefore particularly useful in the treatment of disorders of the autoimmune and the neuronal system. The present invention is furthermore related to novel benzazole derivatives as well as to methods for their preparation and pharmaceutical compositions containing them.

BACKGROUND OF THE INVENTION

Apoptosis denotes the complex contortions of the membrane and organelles of a cell as it undergoes the process of programmed cell death. During said process, the cell activates an intrinsic suicide program and systematically destroys itself. The following series of events can be observed:

The cell surface begins to bleb and expresses pro-phagocytic signals. The whole apoptotic cell then fragments into membrane-bound vesicles that are rapidly and neatly disposed of by phagocytosis, so that there is minimal damage to the surrounding tissue.

The cell then separates from its neighbors.

The nucleus also goes through a characteristic pattern of morphological changes as it commits genetic suicide, the chromatin condenses and is specifically cleaved to fragments of DNA.

Neuronal cell death plays an important role in ensuring that the nervous system develops normally. It appears that the death of developing neurons depends on the size of the target that they innervate: cells with fewer synaptic partners are more likely to die than those which have formed multiple synapses. This may reflect a process, which balances the relative number of pre- to post-synaptic neurons in the developing nervous system Although neuronal cell death was assumed to be apoptotic, it was only recently that neurons in developing rodent brain were conclusively shown to undergo apoptosis as classified by morphology and DNA fragmentation. As cell death during development is clearly not a pathological process, it makes sense that cells actually cease to exist.

Neuronal death occurs via either apoptotic or necrotic processes following traumatic nerve injury or during neurodegenerative diseases. Multiple components are emerging as key players having a role in driving neuronal programmed cell death. Amongst the components leading to neuronal apoptosis are members of the SAPK/JNK being a subfamily of MAP Kinases (MAPKs).

MAPKs (mitogen-activated protein kinases) are serine/threonine kinases that are activated by dual phosphorylation on threonine and tyrosine residues. In mammalian cells, there are at least three separate but parallel pathways that convey information generated by extracellular stimuli to the MAPKs. Said pathways consist of kinase cascades leading to activation of the ERKs (extracellular regulated kinases), the JNKs (c-Jun N-terminal kinases), and the p38/CSBP kinases. While both the JNK and p38 pathways are involved in relaying stress-type extramolecular signals, the ERK pathway is primarily responsible for transducing mitogenic/differentiation signals to the cell nucleus.

SAPK cascades represent a sub-family of the mitogen-activating protein kinase family, that are activated by different external stimuli including DNA damage following UV irradiation, TNF-α, II-1β, ceramide, cellular stress, and reactive oxygen species and have distinct substrate specificities. Signal transduction via MKK4/JNK or MKK3/p38 results in the phosphorylation of inducible transcription factors, c-Jun and ATF2, which then act as either homodimers or heterodimers to initiate transcription of down-stream effectors.

c-Jun is a protein that is forming homodimers and heterodimers (with e.g. c-Fos) to produce the transactivating complex AP-1 which is required for the activation of many genes (e.g. matrix metalloproteinases) involved in the inflammatory response. The JNKs were discovered when it was found that several different stimuli such as UV light and TNF-α stimulated phosphorylation of c-Jun on specific serine residues in the N-terminus of the protein.

In a recent publication of Xie X et al, (*Structure* 1998, 6 (8); 983-991) it has been suggested that activation of stress-activated signal transduction pathways are required for neuronal apoptosis induced by NGF withdrawal in rat PC-12 and superior cervical ganglia (SCG) sympathetic neuronal cells. Inhibition of specific kinases, namely MAP kinase kinase 3 (MKK) and MAP kinase kinase 4 (MKK4), or c-Jun (part of the MKK-4 cascade) may be sufficient to block apoptosis (see also Kumagae Y et al, in *Brain Res Mol Brain Res*, 1999, 67(1), 10-17 and Yang DD et al in *Nature*, 1997, 389 (6653); 865-870). Within a few hours of NGF deprivation in SCG neurones, c-Jun becomes highly phosphorylated and protein levels increase. Similarly in rat PC-12 cells deprived of NGF, JNK and p38 undergo sustained activation while ERKs are inhibited. Consistent with this JNK3 KO mice are resistant to excitotoxicity induced apoptosis in the hippocampus and more importantly they display greatly reduced epileptic like seizures in response to excitotoxicity as compared to normal animals (*Nature* 1997, 389, 865-870).

More recently, it has been reported that the JNK signalling pathway is implicated in cell proliferation and could play an important role in autoimmune diseases (*Immunity*, 1998, 9, 575-585; *Current Biology*, 1999, 3, 116-125) which are mediated by T-cell activation and proliferation.

Naive (precursor) CD4$^+$ helper T (Th) cells recognise specific MHC-peptide complexes on antigen-presenting cells (APC) via the T-cell receptor (TCR) complex. In addition to the TCT-mediated signal, a costimulatory signal is provided at least partially by the ligation of CD28 expressed on Tells with B7 proteins on APC. The combination of these two signals induces T-cell clonal expression.

After 4-5 days of proliferation, precursor of CD4$^+$ T cells differentiate into armed effector Th cells that mediate the functions of the immune system. During the differentiation process, substantial reprogramming of gene expression occurs.

Two subsets of effector Th cells have been defined on the basis of their distinct cytokine secretion pattern and their immunomodulatory effects: Th1 cells produce IFNγ and LT (TNF-β), which are required for cell-mediated inflammatory reactions; Th2 cells secrete IL-4, IL-5, IL-6, IL-10 and IL-13, which mediate B cell activation and differentiation. These cells play a central role in the immune response. The JNK MAP Kinase pathway is induced in Th1 but not in Th2 effector cells upon antigen stimulation. Furthermore, the differentiation of precursor CD4+ T cells into effector Th1 but not Th2 cells is impaired in JNK2-deficient mice. Therefore, in recent years it has been realized that the JNK kinase pathway plays an important role in the balance of Th1 and Th2 immune response through JNK2.

With the objective of inhibiting the JNK kinase pathway, WO/9849188 teaches the use of a human polypeptide, i.e. JNK-interacting protein 1 (JIP-1), which is a biological product and which has also been assayed for overcoming apoptosis related disorders.

Although such human polypeptides have been confirmed to have an inhibitory effect onto the JNK kinase pathway, a whole variety of drawbacks are associated with their use:

The preparation of peptides or proteins may be expensive.
The peptides or proteins may display poor membrane penetration and may not cross the blood brain membrane,
The oral administration of peptides or proteins may not be available because of decomposition through hydrolysis by the acid medium of the stomach.
Peptides or proteins may cause an autoimmune response.

Hence, it was an objective of the present invention to provide relatively small molecules that avoid essentially all of the above-mentioned drawbacks arising from the use of bio-peptides or bio-proteins, however, which are suitable for the treatment of a variety of diseases, in particular of neuronal or the autoimmune system related disorders. It was notably an objective of the present invention to provide relatively small molecule chemical compounds being able to modulate, preferably to down-regulate or to inhibit the JNK (Jun kinase) pathway so to be available as a convenient method of treating a host of diseases. Moreover, it was an objective of the present invention to provide methods for preparing said small molecule chemical compounds. It was furthermore an objective of the present invention to provide a new category of pharmaceutical formulations for the treatment of a host of diseases. It was finally an objective of the present invention to provide a method of treating diseases that are caused by disorders of the autoimmune and/or the neuronal system.

DESCRIPTION OF THE INVENTION

The aforementioned objectives have been met according to the independent claims. Preferred embodiments are set out within the dependent claims which are incorporated herewith.

The following paragraphs provide definitions of the various chemical moieties that make up the compounds according to the invention and are intended to apply uniformly throughout the specification and claims unless an otherwise expressly set out definition provides a broader definition.

"$C_1$-$C_6$-alkyl" refers to monovalent alkyl groups having 1 to 6 carbon atoms. This term is exemplified by groups such as methyl, ethyl, n-propyl, isopropyl, n-butyl isobutyl, tert-butyl, n-hexyl and the like.

"Aryl" refers to an unsaturated aromatic carbocyclic group of from 6 to 14 carbon atoms having a single ring (e.g. phenyl) or multiple condensed rings (e.g. naphthyl). Preferred aryl include phenyl, naphthyl, phenantrenyl and the like.

"$C_1$-$C_6$-alkyl aryl" refers to $C_1$-$C_6$-alkyl groups having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido [3,2-b]pyridyl, pyrido [4,3-b]pyridyl, quinolyl, isoquinolyl, tetrazolyl, 5,6,7,8-tetrahydroquinolyl, 5,6,7,8-tetra-hydroisoquinolyl, purinyl, pteridinyl, carbazolyl, xanthenyl or benzoquinolyl.

"$C_1$-$C_6$-alkyl heteroaryl" refers to $C_1$-$C_6$-alkyl groups having a heteroaryl substituent, including 2-furylmethyl, 2-thienylmethyl, 2-(1H-indol-3-yl)ethyl and the like.

"Alkenyl" refers to alkenyl groups preferably having from 2 to 6 carbon atoms and having at least 1 or 2 sites of alkenyl unsaturation. Preferable alkenyl groups include ethenyl (—CH=$CH_2$), n-2-propenyl (allyl, —$CH_2$CH=$CH_2$) and the like.

"Alkynyl" refers to alkynyl groups preferably having from 2 to 6 carbon atoms and having at least 1-2 sites of alkynyl unsaturation, preferred alkynyl groups include ethynyl (—C≡CH), propargyl (—$CH_2$C≡CH), and the like.

"Acyl" refers to the group —C(O)R where R includes "$C_1$-$C_6$-alkyl", "aryl", "heteroaryl", "$C_1$-$C_6$-alkyl aryl" or "$C_1$-$C_6$-alkyl heteroaryl".

"Acyloxy" refers to the group —OC(O)R where R includes "$C_1$-$C_6$-alkyl", "aryl", "heteroaryl", "$C_1$-$C_6$-alkyl aryl" or "$C_1$-$C_6$-alkyl heteroaryl".

"Alkoxy" refers to the group —O—R where R includes "$C_1$-$C_6$-alkyl" or "aryl" or "heteroaryl" or "$C_1$-$C_6$-alkyl aryl" or "$C_1$-$C_6$-alkyl heteroaryl". Preferred alkoxy groups include by way of example, methoxy, ethoxy, phenoxy and the like.

"Alkoxycarbonyl" refers to the group —C(O)OR where R includes "$C_1$-$C_6$-alkyl" or "aryl" or "heteroaryl" or "$C_1$-$C_6$-alkyl aryl" or "$C_1$-$C_6$-alkyl heteroaryl".

"Aminocarbonyl" refers to the group —C(O)NRR' where each R, R' includes independently hydrogen or $C_1$-$C_6$-alkyl or aryl or heteroaryl or "$C_1$-$C_6$-alkyl aryl" or "$C_1$-$C_6$-alkyl heteroaryl".

"Acylamino" refers to the group —NR(CO)R' where each R, R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl".

"Halogen" refers to fluoro, chloro, bromo and iodo atoms.

"Sulfonyl" refers to group "—$SO_2$—R" wherein R is selected from H, "aryl", "heteroaryl", "$C_1$-$C_6$-alkyl", "$C_1$-$C_6$-alkyl" substituted with halogens e.g. an —$SO_2$—$CF_3$ group, "$C_1$-$C_6$-alkyl aryl" or "$C_1$-$C_6$-alkyl heteroaryl".

"Sulfoxy" refers to a group "—S(O)—R" wherein R is selected from H, "$C_1$-$C_6$-alkyl", "$C_1$-$C_6$-alkyl" substituted with halogens e.g. an —SO—$CF_3$ group, "aryl", "heteroaryl", "$C_1$-$C_6$-alkyl aryl" or "$C_1$-$C_6$-alkyl heteroaryl".

"Thioalkoxy" refers to groups —S—R where R includes "$C_1$-$C_6$-alkyl" or "aryl" or "heteroaryl" or "$C_1$-$C_6$-alkyl aryl" or "$C_1$-$C_6$-alkyl heteroaryl". Preferred thioalkoxy groups include thiomethoxy, thioethoxy, and the like.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "$C_1$-$C_6$-alkyl", "$C_1$-$C_6$-allyl aryl", "$C_1$-$C_6$- alkyl heteroaryl", "$C_2$-$C_6$-alkenyl", "$C_2$$C_6$-alkynyl", primary, secondary or tertiary amino groups or quarter-nary ammonium moieties, "acyl", "acyloxy", "acylamino", "aminocarbonyl", "alkoxycarbonyl", "aryl", "heteroaryl", carboxyl, cyano, halogen, hydroxy, mercapto, nitro, sulfoxy, sulfonyl, alkoxy, thioalkoxy, trihalomethyl and the like. Alternatively said substitution could also comprise situations where neighboring substituents have undergone ring closure, notably when viccinal functional substituents are involved, thus forming e.g. lactams, lactons, cyclic anhydrides, but also acetals, thioacetals, aminals formed by ring closure for instance in an effort to obtain a protective group.

"Pharmaceutically acceptable salts or complexes" refers to salts or complexes of the below-identified compounds of formula I that retain the desired biological activity. Examples of such salts include, but are not restricted to acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and polygalacturonic acid. Said compounds can also be administered as pharmaceutically acceptable quaternary salts known by a person skilled in the art, which specifically include the quarternary ammonium salt of the formula —NR,R',R"+Z−, wherein R, R', R" is independently hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate). Sample based-addition salts include those derived from sodium, potassium, ammonium, and quaternary ammonium hydroxide, such as for example tetramethylammonium hydroxide.

"Pharmaceutically active derivative" refers to any compound that upon administration to the recipient, is capable of providing directly or indirectly, the activity disclosed herein. "Enantiomeric excess" (ee) refers to the products that are obtained by an essentially enantiomeric synthesis or a synthesis comprising an enantioselective step, whereby a surplus of one enantiomer in the order of at least about 52% ee is yielded. In the absence of an enantiomeric synthesis, racemic products are usually obtained that do however also have the inventive set out activity as of JunKinases inhibitors.

It was now found that benzazole derivatives according to formula I are suitable pharmaceutically active agents, by modulating, in particular by inhibiting the action of JNK's, notably of JNK 2 and/or 3.

The compounds according to the present invention are those of formula I.

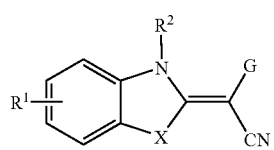

I

In the compounds according to formula I
X is O, S or $NR^0$, with $R^0$ being H or an unsubstituted or substituted $C_1$-$C_6$ alkyl. Most preferred is X=S.

G is an unsubstituted or substituted or fused pyrimidinyl group.

$R^1$ is selected from the group comprising or consisting of hydrogen, unsubstituted or substituted $C_1$-$C_6$-alkoxy, unsubstituted or substituted $C_1$-$C_6$-thioalkoxy, unsubstituted or substituted $C_1$-$C_6$-alkyl, unsubstituted or substituted $C_2$-$C_6$-alkenyl, unsubstituted or substituted $C_2$-$C_6$-alkynyl, primary, secondary or tertiary amino groups, aminoacyl, aminocarbonyl, unsubstituted or substituted $C_1$-$C_6$ alkoxycarbonyl, unsubstituted or substituted aryl, unsubstituted or substituted heteroaryl, carboxyl, cyano, halogen, hydroxy, nitro, sulfoxy, sulfonyl, sulfonamide, unsubstituted or substituted hydrazides.

Most preferred substituents $R^1$ are hydrogen, halogen, $C_1$-$C_6$-alkyl and $C_1$-$C_6$ alkoxy groups.

$R^2$ is selected from the group comprising or consisting of hydrogen, unsubstituted or substituted $C_1$-$C_6$-alkyl, unsubstituted or substituted $C_2$-$C_6$-alkenyl, unsubstituted or substituted $C_2$-$C_6$-alkynyl, unsubstituted or substituted $C_1$-$C_6$-alkyl-aryl, unsubstituted or substituted aryl or heteroaryl, unsubstituted or substituted $C_1$-$C_6$-alkyl-heteroaryl, —C(O)—$OR^3$, —C(O)—$R^3$, —C(O)$NR^3R^{3'}$, —($SO_2$)$R^3$, whereby $R^3$ and $R^{3'}$ are independently selected from the group comprising or consisting of hydrogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted aryl, unsubstituted or substituted heteroaryl, unsubstituted or substituted $C_1$-$C_6$-alkyl aryl, unsubstituted or substituted $C_1$-$C_6$-alkyl heteroaryl.

The present invention also includes the tautomers, its geometrical isomers, the optical active forms, enantiomers, diastereomers of compounds according to formula I as well as their racemates and also pharmaceutically acceptable salts, as well as the pharmaceutically active derivatives of benzazole of formula I.

Preferred substituents $R^2$ are hydrogen, unsubstituted or substituted $C_1$-$C_6$ alkyl, unsubstituted or substituted $C_1$-$C_6$ alkylaryl or $C_1$-$C_6$ alkylheteroaryl group, —C(O)—$R^3$, —C(O)—$NR^3R^{3'}$, —($SO_2$)$R^3$, whereby $R^3$ and $R^{3'}$ are as above defined. More preferred substituents $R^2$ are hydrogen and $C_1$-$C_6$-alkyl groups, whereby $R^2$=H is the most preferred embodiment.

Preferred $R^3$ and $R^{3'}$ are hydrogen, $C_1$-$C_6$ alkyl aryl, heteroaryl, $C_1$-$C_6$-alkyl aryl, $C_1$-$C_6$-alkyl heteroaryl. Most preferred $R^3$ and $R^{3'}$ is hydrogen or $C_1$-$C_6$ alkyl.

Such tautomers mentioned herein are only those wherein $R^2$ and/or $R^0$ are hydrogen and which display the formula II, more specifically formula IIa and IIb. Said tautomers undergo transformation in solution and an equilibrium between the benzazoles of formula Ia and Ib is established with those of formula IIa and IIb.

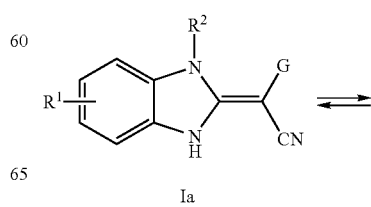

Ia

-continued

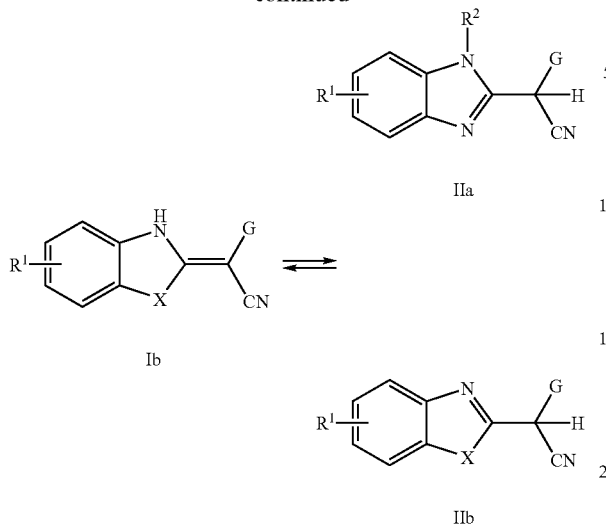

Said tautomers are comprised by the present application.

Basically, all of the above mentioned aryl or heteroaryl substituents could optionally be ether substituted by at least one of the groups selected from substituted or unsubstituted $C_1$-$C_6$-alkyl, like trihalomethyl, substituted or unsubstituted $C_1$-$C_6$-alkoxy, acetoxy, substituted or unsubstituted $C_2$-$C_6$-alkenyl, substituted or unsubstituted $C_2$-$C_6$-alkynyl, amino, aminoacyl, aminocarbonyl, $C_1$-$C_6$-alkoxycarbonyl, aryl, carboxyl, cyano, halogen, hydroxy, nitro, sulfonyl, sulfoxy, $C_1$-$C_6$-thioalkoxy. Preferably said aryl or heteroaryl groups are substituted by halogen, hydroxy, nitro, sulfonyl, e.g. a trifluoromethylsulfonyl group.

Particularly preferred benzazole derivatives are those wherein G is an unsubstituted or substituted pyrimidinyl group which are linked to the benzazole acetate scaffold via the position 4

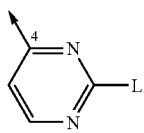

wherein L is selected from the group comprising or consisting of hydrogen, unsubstituted or substituted $C_1$-$C_6$ alkyl, unsubstituted or substituted $C_1$-$C_6$ alkoxy, unsubstituted or substituted $C_1$-$C_6$ thioalkoxy, unsubstituted or substituted $C_2$-$C_6$ alkenyl, unsubstituted or substituted $C_2$-$C_6$ alkynyl, primary, secondary or tertiary amino groups, aminoacyl, aminocarbonyl, amino-($C_1$-$C_{10}$)alkyl, amino-unsubstituted or substituted ($C_1$-$C_{10}$)-alkyl-aryl, amino-unsubstituted or substituted ($C_1$-$C_{10}$)alkyl-heteroaryl, unsubstituted or substituted $C_1$-$C_6$ alkoxycarbonyl, carboxyl, cyano, halogen, hydroxy, nitro, sulfoxy, sulfonyl, unsubstituted or substituted aryl, unsubstituted or substituted heteroaryl, unsubstituted or substituted 3-8 membered cycloalkyl, optionally containing at least one heteroatom selected from N, O, S, and unsubstituted or substituted hydrazido groups.

Particularly preferred benzazole derivatives are those wherein L is a substituted or unsubstituted ($C_1$-$C_{10}$)-alkyl group.

Further particularly preferred benzazole derivatives are those wherein L is a group —N($R^a$, $R^b$) or —O$R^a$, with $R^a$ and $R^b$ being each independently selected from the group consisting of H, unsubstituted or substituted ($C_1$-$C_{10}$)-alkyl, unsubstituted or substituted $C_1$-$C_6$ alkyl-aryl, unsubstituted or substituted $C_1$-$C_6$-alkyl-heteroaryl, unsubstituted or substituted aryl or heteroaryl and unsubstituted or substituted 48 membered saturated or unsaturated cycloalkyl.

Pursuant to a particularly preferred embodiment according to formula I L is selected from

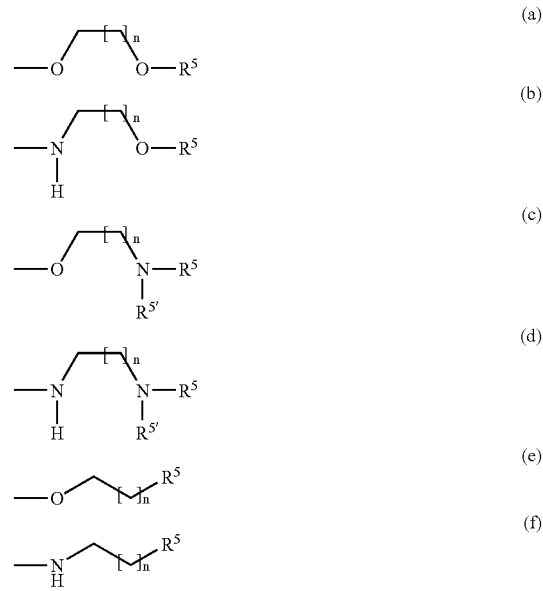

wherein n is 1 to 10, preferably 1 to 6, while X is preferably S, $R^1$ is H and $R^2$ is H.

$R^5$ and $R^{5'}$ are independently selected from each other from the group consisting of H, substituted or unsubstituted $C_1$-$C_{10}$alkyl, substituted or unsubstituted aryl or heteroaryl, substituted or unsubstituted $C_1$-$C_6$alkyl-aryl and substituted or unsubstituted $C_1$-$C_6$-alkyl-heteroaryl. Most preferred $R^{5'}$ is an unsubstituted or substituted imidazolyl.

The most further preferred benzazole derivatives according to formula I are benzothiazole acetonitrile derivatives of the formula Ib and/or its tautomers of formula IIb

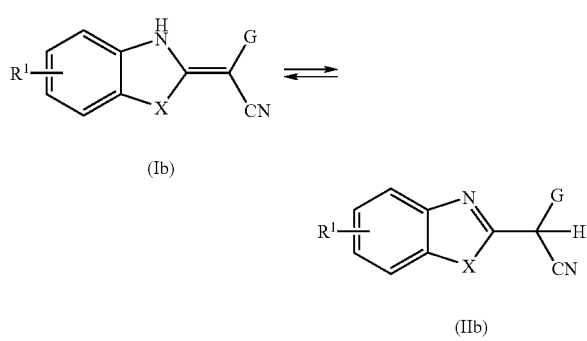

wherein X is S, $R^1$ is H or $C_1$-$C_6$ alkyl and $R^2$ is H, while G is a pyrimidinyl group of the formula

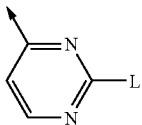

with L being either

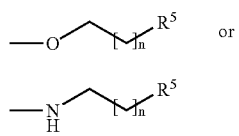

wherein n is 0, 1 or 2 and $R^5$ is an aryl or heteroaryl, in particular substituted or unsubstituted phenyl, substituted or unsubstituted pyridyl, substituted or unsubstituted imidazolyl.

Specific examples of compounds of formula I include the following:
1,3-benzothiazol-2-yl(2-chloro-4-pyrimidinyl)acetonitrile
1,3-benzothiazol-2-yl(2,6dimethoxy-4-pyrimidinyl)acetonitrile
1,3-benzothiazol-2-yl(2-chloro6-methyl4pyrimidinyl)acetonitrile
1,3-benzothiazol-2-yl[2-(methylsulfanyl)-4-pyrimidinyl]acetonitrile
1,3-benzothiazol-2-yl{6-chloro-5-nitro-4-pyrimidinyl}acetonitrile
1,3-benzothiazol-2-yl(2-hydroxy-pyrimidin-4-yl)acetonitrile
(2chloropyrimidin-4yl)[5-(trifluoromethyl)-1,3-benzothiazol-2-yl]acetonitrile
(2E)-(2-chloro-4-pyrimidinyl)(3-methyl-1,3-benzothiazol-2(3H)-ylidene)ethanenitrile
1,3-benzothiazol-2-yl(2-{[2-(1H-imidazol-5-yl)ethyl]amino}-4-pyrimidinyl)acetonitrile
1,3-benzothiazol-2-yl[2-(1-piperazinyl)-4-pyrimidinyl]acetonitrile
1,3-benzothiazol-2-yl[2-(4-benzyl-1-piperidinyl)-4-pyrimidinyl]acetonitrile
1,3-benzothiazol-2-yl[2-(4-methyl-1-piperazinyl)-4pyrimidinyl]acetonitrile
1,3-benzothiazol-2-yl[2-(4-morpholinyl)-4-pyrimidinyl]acetonitrile
1,3-benzothiazol-2-yl[2-(methylamino)-4-pyrimidinyl]acetonitrile
1,3-benzothiazol-2-yl(2-{4-[2-(4-morpholinyl)ethyl]-1-piperazinyl}-4-pyrimidinyl)-acetonitrile
1,3-benzothiazol-2-yl{2-[4-(benzyloxy)-1-piperidinyl]-4pyrimidinyl}acetonitrile
1,3-benzothiazol-2-yl[2-(4hydroxy-1-piperidinyl)-4-pyrimidinyl]acetonitrile
1,3-benzothiazol-2-yl(2-hydrazino-4-pyrmidinyl)acetonitrile
1,3-benzothiazol-2-yl(2-{[2-(dimethylamino)ethyl]amino}-4-pyrimidinyl)acetonitrile
1,3-benzothiazol-2-yl[2-(dimethylamino)-4-pyrimidinyl]acetonitrile
1,3-benzothiazol-2-yl{2-[(2-methoxyethyl)amino]-4-pyrimidinyl}acetonitrile
1,3-benzothiazol-2-yl{2-[(2-hydroxyethyl)amino]-4-pyrimidinyl}acetonitrile
1,3-benzothiazol-2-yl[2-propylamino)-4-pyrimidinyl]acetonitrile
1,3-benzothiazol-2-yl(2-{[3-(1H-imidazol-1-yl)propyl]amino}-4-pyrimidinyl)acetonitrile
1,3-benzothiazol-2-yl[2-(1-pyrrolidinyl)4-pyrimidinyl]acetonitrile
1,3-benzothiazol-2-yl{2-[(2-phenylethyl)amino]-4-pyrimidinyl}acetonitrile
1,3-benzothiazol-2-yl(2-{[2-(2-pyridinyl)ethyl]amino}-4-pyrimidinyl)acetonitrile
1,3-benzothiazol-2-yl{2-[(2-pyridinylmethyl)amino]-4-pyrimidinyl}acetonitrile
1,3-benzothiazol-2-yl{2-[4-(1H-1,2,3-benzothiazol-1-yl)-1-piperidinyl]-4-pyrimidinyl}acetonitrile
1,3-benzothiazol-2-yl{2-[4-(2-pyrazinyl)-1-piperazinyl]-4-pyrimidinyl}acetonitrile
1,3-benzothiazol-2-yl{2-[4-(2-pyrimidinyl)-1-piperazinyl]-4-pyrimidinyl}acetonitrile
1,3-benzothiazol-2-yl(2-{[2-(3-pyridinyl)ethyl]amino}-4-pyrimidinyl)acetonitrile
1,3-benzothiazol-2-yl(5-bromo-2-{[2-(dimethylamino)ethyl]amino}-4-pyrimidinyl)-acetonitrile
1,3-benzothiazol-2-yl{2-[(2-morpholin-4ylethyl)amino]pyrimidin-4-yl}acetonitrile
1,3-benzothiazol-2-yl[2-(4-{3-[(trifluoromethyl)sulfonyl]anilino}piperidin-1-yl)pyrimidin-4-yl]acetonitrile
1,3-benzothiazol-2-yl(2-{[3-(2-oxopyrrolidin-1-yl)propyl]amino}pyrimidin-4-yl)-acetonitrile
1,3-benzothiazol-2-yl(2-{methyl[3-(methylamino)propyl]amino}pyrimidin-4-yl)acetonitrile
1,3-benzothiazol-2-yl(2-{[3-(4-methylpiperazin-1-yl)propyl]amino}pyrimidin-4-yl)-acetonitrile
1,3-benzothiazol-2-yl{2-[(3-morpholin-4-ylpropyl)amino]pyrimidin-4yl}acetonitrile
1,3-benzothiazol-2-yl(2-{[2-(1-methyl-1H-imidazol-4-yl)ethyl]amino}pyrimidin-4-yl)acetonitrile
1,3-benzothiazol-2-yl(2-{[2-(1H-indol-3-yl)ethyl]amino}pyrimidin-4-yl)acetonitrile
1,3-benzothiazol-2-yl(2-{[2-(4hydroxyphenyl)ethyl]amino}pyrimidin-4-yl)acetonitrile
tert-butyl ({4-[1,3-benzothiazol-2-yl(cyano)methyl]pyrimidin-2-yl}amino)acetate
{2-[(3-aminopropyl)amino]pyrimidin-4-yl}(1,3-benzothiazol-2-yl)acetonitrile
{2-[(2-aminoethyl)amino]pyrimidin-4-yl}(1,3-benzothiazol-2-yl)acetonitrile
1,3-benzothiazol-2-yl(2-{[3-(dimethylamino)propyl]amino}pyrimidin-4-yl)acetonitrile
1,3-benzothiazol-2-yl {2-[(2-piperidin-1-ylethyl)amino]pyrimidin-4-yl}acetonitrile
1,3-benzothiazol-2-yl(2-{[2-(1-methyl-1H-imidazol-5-yl)ethyl]amino}pyrimidin-4-yl)acetonitrile
1,3-benzothiazol-2-yl[2-(benzylamino)pyrimidin-4-yl]acetonitrile
isopropyl 3-({4-[1,3-benzothiazol-2-yl(cyano)methyl]pyrimidin-2-yl}amino)propanoate
1,3-benzothiazol-2-yl{2-[(3-hydroxypropyl)amino]pyrimidin-4-yl}acetonitrile
1,3-benzothiazol-2-yl{2-[(pyridin-3-ylmethyl)amino]pyrimidin-4-yl}acetonitrile
(2-aminopyrimidin-4-yl)(1,3-benzothiazol-2-yl)acetonitrile
1,3-benzothiazol-2-yl{2-[(pyridin-4-ylmethyl)amino]pyrimidin-4-yl}acetonitrile
tert-butyl 4-[2-({4-[1,3-benzothiazol-2-yl(cyano)methyl]pyrimidin-2-yl}amino)-ethyl]phenylcarbamate (2-{[2-(4-aminophenyl)ethyl]amino}pyrimidin-4-yl)(1,3-benzothiazol-2-yl)acetonitrile
1,3-benzothiazol-2-yl(2-{[2-(3,4-dimethoxyphenyl)ethyl]amino}pyrimidin-4-yl)acetonitrile
1,3-benzothiazol-2-yl(2-{[2-(3-methoxyphenyl)ethyl]amino}pyrimidin-4-yl)acetonitrile
1,3-benzothiazol-2-yl(2-{[2-(2-fluorophenyl)ethyl]amino}pyrimidin-4-yl)acetonitrile
1,3-benzothiazol-2-yl[2-({2-[3-(trifluoromethyl)phenyl]ethyl}amino)pyrimidin-4-yl]acetonitrile
1,3-benzothiazol-2-yl{2-[(2-hydroxy-2-phenylethyl)amino]pyrimidin-4-yl}acetonitrile
1,3-benzothiazol-2-yl{2-[(2-{[3-(trifluoromethyl)pyridin-2-yl]amino}ethyl)amino]-pyrimidin-4-yl}acetonitrile
1,3-benzothiazol-2-yl(2-{[2-(3-chlorophenyl)ethyl]amino}pyrimidin-4-yl)acetonitrile
1,3-benzothiazol-2-yl(2-{[2-(3,4-dichlorophenyl)ethyl]amino}pyrimidin-4-yl)acetonitrile
1,3-benzothiazol-2-yl(2-{[2-(4-methoxyphenyl)ethyl]amino}pyrimidin-4-yl)acetonitrile
1,3-benzothiazol-2-yl(2-{[2-(4-methylphenyl)ethyl]amino}pyrimidin-4-yl)acetonitrile
1,3-benzothiazol-2-yl(2-{[2-(3-fluorophenyl)ethyl]amino}pyrimidin-4-yl)acetonitrile
1,3-benzothiazol-2-yl(2-{[2-(4-phenoxyphenyl)ethyl]amino}pyrimidin-4-yl)acetonitrile
1,3-benzothiazol-2-yl(2-{[2-(2-phenoxyphenyl)ethyl]amino}pyrimidin-4-yl)acetonitrile
1,3-benzothiazol-2-yl(2-{[2-(4-bromophenyl)ethyl]amino}pyrimidin-4-yl)acetonitrile
1,3-benzothiazol-2-yl(2-{[2-(4-fluorophenyl)ethyl]amino}pyrimidin-4-yl)acetonitrile
1,3-benzothiazol-2-yl{2-[(2-[1,1'-biphenyl]-4-ylethyl)amino]pyrimidin-4-yl}acetonitrile
1,3-benzothiazol-2-yl{2-[(2-{4-[hydroxy(oxido)amino]phenyl}ethyl)amino]pyrimidin-4-yl}acetonitrile
1,3-benzothiazol-2-yl(2-{[2-(1H-1,2,4-triazol-1-yl)ethyl]amino}pyrimidin-4-yl)acetonitrile
1,3-benzothiazol-2-yl(2-{[3-(1H-pyrazol-1-yl)propyl]amino}pyrimidin-4-yl)acetonitrile
4-[2-({4-[1,3-benzothiazol-2-yl(cyano)methyl]pyrimidin-2-yl}amino)ethyl]benzene-sulfonamide
{2-[(2-pyridin-3-ylethyl)amino]pyrimidin-4-yl}[5-(trifluoromethyl)-1,3-benzothiazol-2-yl]acetonitrile
1,3-benzothiazol-2-yl{2-[(1H-tetraazol-5-ylmethyl)amino]pyrimidin-4-yl}acetonitrile
1,3-benzothiazol-2-yl[2-(benzyloxy)pyrimidin-4-yl]acetonitrile
1,3-benzothiazol-2-yl{2-[(4-pyridin-3-ylbenzyl)oxy]pyrimidin-4-yl}acetonitrile
1,3-benzothiazol-2-yl[2-(pyridin-4-ylmethoxy)-4-pyrimidinyl]acetonitrile
1,3-benzothiazol-2-yl[2-(pyridin-2-ylmethoxy)pyrimidin-4-yl]acetonitrile
1,3-benzothiazol-2-yl[2-(3-pyridin-2-ylpropoxy)pyrimidin-4-yl]acetonitrile
1,3-benzothiazol-2-yl{2-[(4-methoxybenzyl)oxy]pyrimidin-4-yl}acetonitrile
1,3-benzothiazol-2-yl[2-(pyridin-3-ylmethoxy)pyrimidin-4-yl]acetonitrile
1,3-benzothiazol-2-yl{2-[2-(4-methoxyphenyl)ethoxy]pyrimidin-4-yl}acetonitrile
1,3-benzothiazol-2-yl[2-([1,1'-biphenyl]-3-ylmethoxy)pyrimidin-4-yl]acetonitrile
1,3-benzothiazol-2-yl{2-[(3,4,5-trimethoxybenzyl)oxy]pyrimidin-4-yl}acetonitrile
1,3-benzothiazol-2-yl{2-[(3,4-dichlorobenzyl)oxy]pyrimidin-4-yl}acetonitrile
1,3-benzothiazol-2-yl[2-({3-[(dimethylamino)methyl]benzyl}oxy)pyrimidin-4-yl]acetonitrile
1,3-benzothiazol-2-yl{2-[(1-oxidopyridin-3-yl)methoxy]pyrimidin-4-yl}acetonitrile
1,3-benzothiazol-2-yl(2-{[4-(morpholin-4-ylmethyl)benzyl]oxy}pyrimidin-4-yl)acetonitrile
1,3-benzothiazol-2-yl{2-[(4pyridin-2-ylbenzyl)oxy]pyrimidin-4-yl}acetonitrile
1,3-benzothiazol-2-yl(2-{[4-(piperidin-1-ylmethyl)benzyl]oxy}pyrimidin-4-yl)acetonitrile
1,3-benzothiazol-2-yl[2-(4-methoxyphenoxy)pyrimidin-4-yl]acetonitrile
1,3-benzothiazol-2-yl[2-(4-butoxyphenoxy)pyrimidin-4-yl]acetonitrile
{2-[4-(4-acetylpiperazin-1-yl)phenoxy]pyrimidin-4-yl}(1,3-benzothiazol-2-yl)acetonitrile
[2-(4-methoxyphenoxy)pyrimidin-4-yl][5-(trifluoromethyl)-1,3-benzothiazol-2-yl]acetonitrile
1,3-benzothiazol-2-yl(pyrimidin-4-yl)acetonitrile
N-[2-({4-[1,3-benzothiazol-2-yl(cyano)methyl]pyrimidin-2-yl}amino)ethyl]-4-chlorobenzene
1,3-benzothiazol-2-yl(2-methoxy-4-pyrimidinyl)acetonitrile Thereby, the most preferred compounds are those which are selected from the group consisting of:
1,3-benzothiazol-2-yl(2-chloro-4-pyrimidinyl)acetonitrile
1,3-benzothiazol-2-yl[2-(methylsulfanyl)-4-pyrimidinyl]acetonitrile
1,3-benzothiazol-2-yl(2-{[2-(1H-imidazol-5-yl)ethyl]amino}-4-pyrimidinyl)acetonitrile
1,3-benzothiazol-2-yl[2(methylamino)-4-pyrimidinyl]acetonitrile
1,3-benzothiazol-2-yl{2-[(2-hydroxyethyl)amino]-4-pyrimidinyl}acetonitrile
1,3-benzothiazol-2-yl[2-(benzyloxy)pyrimidin-4-yl]acetonitrile
1,3-benzothiazol-2-yl[2-(4-methoxyphenoxy)pyrimidin-4-yl]acetonitrile
1,3-benzothiazol-2-yl(2-methoxy-4-pyrimidinyl)acetonitrile
1,3-benzothiazol-2-yl(2-{[2-(3-pyridinyl)ethyl]amino}-4-pyrimidinyl)acetonitrile A total of 12 compounds falling into formula I and II have been disclosed in a catalogue of the company Maybridge plc. In three of said compounds X is S, $R^1$ and $R^2$ is H and G is

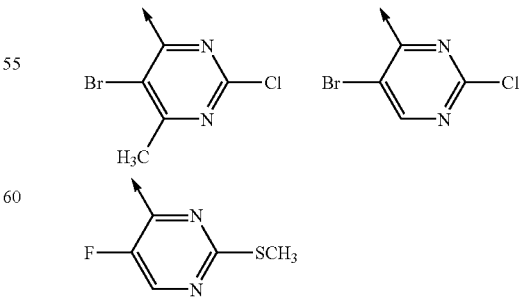

In three more compounds of Maybridge X is NH $R^1$ and $R^2$ are H, G is either of the following pyrimidines:

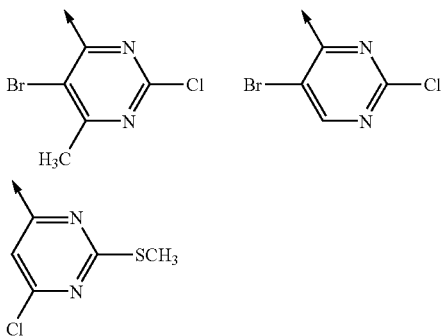

Finally, in six Maybridge compound X is N—CH$_3$, R$^1$ and R$^2$ are H and G is either of the following pyrimidines:

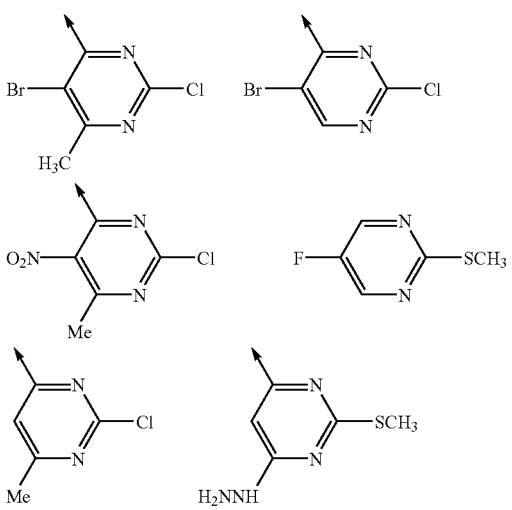

A further aspect of the present invention is related to the use of the benzazole derivatives according to formula I for the preparation of pharmaceutical compositions for the modulation—notably of the inhibition—of the JNK pathway associated disorders, in particular of neuronal disorders and/or of disorders of the immune system as well as said pharmaceutical compositions themselves. Preferred JNK pathways are those involving JNK2 and/or JNK3.

As pointed out above, the compounds of formula I are suitable to be used as a medicament. Hence, it is herein reported the compounds of formula I and its tautomers are suitable for use in treating a whole variety of diseases. Said diseases include disorders of the autoimmune system and neuronal system of mammals, notably of human beings. More specifically, the compounds according to formula I, alone or in the form of a pharmaceutical composition, are useful for the modulation of the JNK pathway, more specifically for the treatment or prevention of disorders associated with abnormal expression or activity of JNK, notably of JNK2 and/or 3. Such an abnormal expression or activity of JNK could be triggered by numerous stimuli (e.g. stress, septic schock, oxidative stress, cytokines) and could lead to out-of-control apoptosis or autoimmune diseases that is frequently involved in the below enumerated disorders and diseases. Hence, the compounds according to formula I could be used for the treatment of disorders by modulating the JNK pathways. Said modulation of the JNK pathway could involve its activation, but preferably it involves the inhibition of the JNK pathways, notably of the JNK2 and/or 3. The compounds according to formula I could be employed alone or in combination with further pharmaceutical agents.

Specifically, the compounds pursuant to formula I are useful for the treatment and/or prevention of immuno- and/or neuronal-related diseases or pathological states in which inhibition of JNK2 and/or JNK3 plays a role such as epilepsy; neurodegenerative diseases including Alzheimer's disease, Huntington's disease, Parkinson's disease; retinal diseases; spinal cord injury head trauma, autoimmune diseases including multiple sclerosis, inflammatory bowel disease (IBD), rheumatoid arthritis; asthma; septic shock; transplant rejection; cancers including breast, colorectal, pancreatic and cardiovascular diseases including stroke, cerebral ischemia, arterosclerosis, myocordial infarction, myocordial reperfusion injury.

Quite surprisingly it turned out that the compounds according to formula I do show a considerable activity as inhibitors of JNK2 and/or 3. According to a preferred embodiment, the compounds according to the invention are essentially inactive in view of 2 further MAP Kinases, i.e. p38 and/or ERK2, belonging incidentally to the same family as JNK2 and 3. Hence, the compounds according to the present invention offer the possibility to selectively modulate the JNK pathway, and in particular to come to grips with disorders related to the JNK pathways, while being essentially inactive with regard to other targets like said p38 and ERK2, so that they could indeed be viewed as selective inhibitors. This is of considerable significance, as these related enzymes are generally involved in different disorders, so that for the treatment of a distinct disorder, it is desired to employ a correspondingly selective medicament.

Still a farther object of the present invention is a process for preparing the novel benzothiazole derivatives according to formula I. A general synthetic access to the compounds according to formula I is the following:

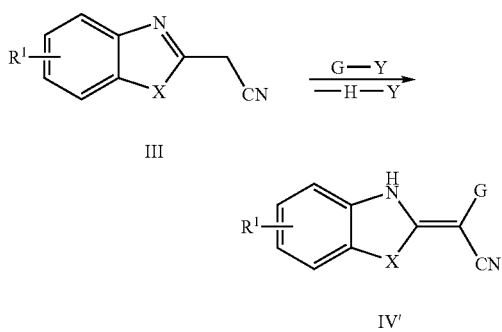

The intermediate compound IV' could be transformed in the following way:

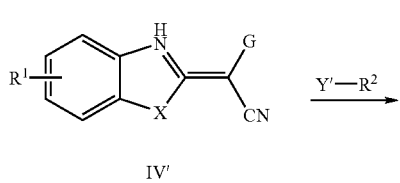

-continued

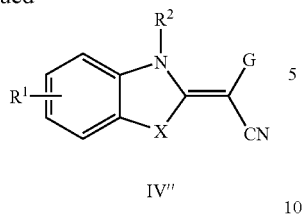

IV'''

The starting material III is thereby reacted with an electrophilic compound G—Y, whereby Y is a suitable leaving group. The choice of Y, Y', the reaction method, the reaction conditions, solvents, catalysts will depend on the nature of G and are appropriately selected according to the knowledge of a person skilled in the art. Said method also comprises any modification of G following condensation of G—Y with compound III.

Preferred compounds of formula I and II are those wherein G is a pyrimidinyl group having the formula:

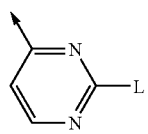

wherein L is as described above. Such compounds are preferably obtained according to the schemes I-III:

Scheme I

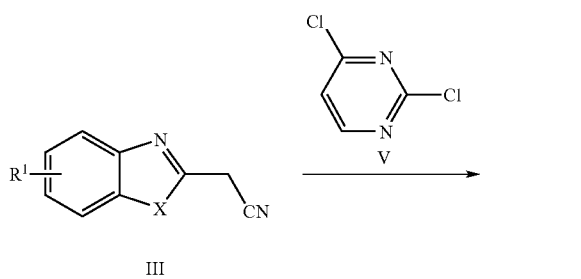

IV

Scheme II

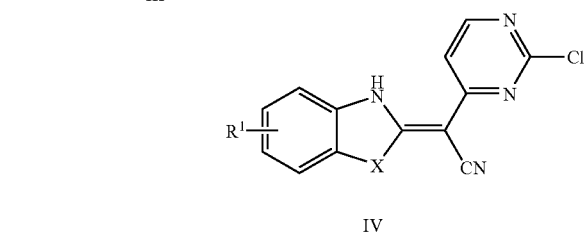

IV

-continued

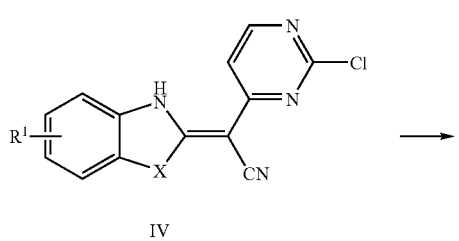

I'

Scheme III

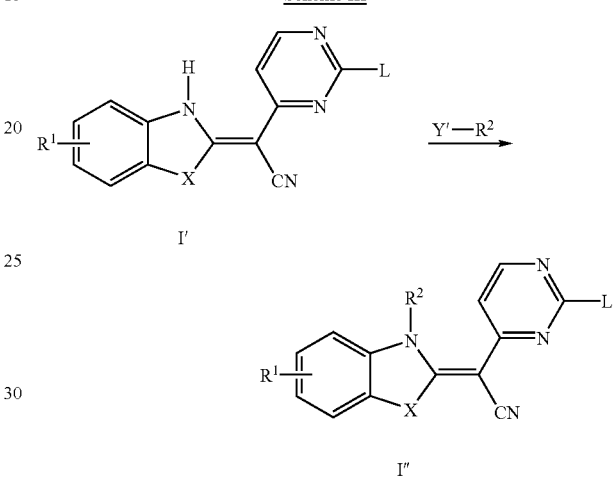

I''

The benzothiazole derivatives can be prepared from readily available staring materials using the following general methods and procedures. It will be appreciated that where typical or preferred experimental conditions (i.e., reaction temperatures, time, moles of reagents, solvents, etc.) are given, other experimental conditions can also be used unless otherwise stated. Optimum reaction conditions may vary with the particular reactants or solvents used, but such conditions can be determined by one skilled in the art by routine optimisation procedures.

In the above schemes I to III, $R^1$, $R^2$ and X are as described above.

In Scheme I the compounds of formula III may be converted to the compounds of formula IV by treatment of the starting compounds with a base such as sodium hydride, potassium hydride and the like in an anhydrous inert atmosphere in polar solvents like DMF or THF at a temperature in the range of about −78° C. to 25° C. (Chabaka L. M. et al, *Pol. J. Chem.* 1994, 1317-1326) for about an hour followed by the drop wise addition of unsubstituted or substituted halogenated pyrmidinyl derivatives of formula V as described above in solvents such as DMF or THF and then gradually warming the mixture to a temperature in the range of about 25° C. to 70° C. for about 1 to 18 hours to afford compounds of formula IV.

Benzazoles of formula III are either commercially available, such as from Maybridge Chemical Co. Ltd or can be prepared from commercially available compounds by conventional procedures, wherein $R^1$ and X are as defined above and are most preferably respectively H and S.

Unsubstituted or substituted halogenated heteroaryl of formula V are also either commercially available, such as from Aldrich, Fluka, Sigma and the like or can be prepared from known compounds by conventional procedures. Preferred halogenated heteroaryl as starting materials include 2,4-dichloropyrimidine, 2-chloropyridine and the like.

In Scheme II the compounds of formula VI, wherein $R^1$, $R^2$ and X are as defined above may be converted to the compounds of formula I" by the treatment with groups of type L, wherein L is as described above. Most preferably, L is an amine, an alcohol or a thioalcohol defined as described above.

The reaction is performed in solution in solvents such as DMF, NMP, DMSO or alcohols for example EtOH, MEOH or iPrOH, most preferably in EtOH, in the presence of an organic base such as $Et_3N$, DIPEA or the like, most preferably $Et_3N$, at a temperature in the range of about 25 to 80° C. In a preferred method, the starting compounds are heated at 70° C. in solution in EtOH in the presence of $Et_3N$.

Amines are either commercially available or can be prepared from known compounds by conventional procedures known by one skilled in the art Preferred amines as starting materials include methylamine, N,N-dimethylaminoethylamine, morpholine histamine and the like.

Alcohols or thioalcohols are either commercially available or can be prepared from known compounds by conventional procedures known by one skilled in the art Preferred alcohols or thioalcohols as starting materials include MeOH, MESH and the like.

In Scheme III the compounds of formula I' wherein $R^2$ is hydrogen and $R^1$ and X are as above described, most preferably H and S, may be converted to the compounds of formula I" wherein $R^2$ is different from hydrogen by the treatment of the starting compound with electrophiles Y'—$R^2$ such as such as alkyl or benzyl halides and acyl chlorides at a temperature in the range of 25° C. to 80° C. in the presence of a base such as potassium carbonate, sodium hydroxide, sodium hydride and the like in a solvent such as DMSO, DMF, acetone and the like in an anhydrous inert atmosphere. In a preferred method, the starting compounds are shaken at 25° C. in solution in DMSO in the presence of potassium carbonate.

Electrophiles are either commercially available or can be prepared from known compounds by conventional procedures known by one skilled in the art. Preferred electrophiles as starting materials include methyl iodide and acetyl chloride.

If the above set out general synthetic methods are not applicable for the obtention of compounds of formula I suitable methods of preparation known by a person skilled in the art should be used.

A final aspect of the present invention is related to the use of the compounds according to formula I for the modulation of the JNK pathway, the use of said compounds for the preparation of pharmaceutical compositions for the modulation of the JNK pathway as well as the formulations containing the active compounds according to formula I. JNK is believed to be involved in numerous disease states. Therefore, modulating the level of JNK, notably of JNK2 and/or JNK3 provides a variety of therapeutic applications, including epilepsy, neurodegenerative diseases including Alzheimer's disease, Huntington's disease, Parkinson's disease; retinal diseases; spinal cord injury; head trauma, autoimmune diseases including multiple sclerosis, inflammatory bowel disease (IBD), rheumatoid arthritis; asthma; septic shock; transplant rejection; cancers including breast, colorectal, pancreatic and cardiovascular diseases including stroke, cerebral ischemia, arterosclerosis, myocordial infarction, myocordial reperfusion injury.

As used herein, "treating" refers to inhibiting or arresting the development of a disease, disorder or condition and/or causing the reduction, remission or regression of the symptoms of a disease, disorder or condition. Those of skill in the art will understand that various methodologies and assays may be used to assess the development of a disease, disorder or condition, and similarly, various methodologies and assays may be used to assess the reduction, remission or regression of the symptoms of a disease, disorder or condition.

As used herein, the term "prevention of disease conditions mediated by JNK" refers to preventing a disease, disorder or condition from occurring in a subject who may be at risk for the disease, but has not yet presented any symptoms thereof Those of skill in the art will understand that a variety of methods may be used to determine a subject at risk for a disease and that whether a subject is at risk for a disease will depend on a variety of factors known to those of skill in the art, including genetic make-up of the patient, age, body weight, sex, diet, general physical and mental health, occupation, exposure to environmental conditions and the like, of the subject.

When employed as pharmaceuticals, the benzazole derivatives of the present invention are typically administered in the form of a pharmaceutical composition. Hence, pharmaceutical compositions comprising a compound of formula I and a pharmaceutically acceptable carrier, diluent or excipient therefore are also within the scope of the present invention. A person skilled in the art is aware of a whole variety of such carrier, diluent or excipient compounds suitable to formulate a pharmaceutical composition. Also, the present invention provides compounds for use as a medicament. In particular, the invention provides the compounds of formula I for use as JNK inhibitor, notably for JNK2 and JNK3, for the treatment of disorders of the immune as well as the neuronal system of mammals, notably of humans, either alone or in combination with other medicaments.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the benzazole derivatives of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of these inventions can be administered by a variety of routes including oral, rectal, transdermal, subcutaneous, intravenous, intramuscular, intrathecal, intraperitoneal and intranasal. Depending on the intended route of delivery, the compounds are preferably formulated as either injectable, topical or oral compositions. The compositions for oral administration may take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the benzazole compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art As above mentioned, the benzazole derivatives of formula I in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 8 of *Remington's Pharmaceutical Sciences,* 17$^{th}$ Edition, 1985, Marck Publishing Company, Easton, Pa., which is incorporated herein be reference.

The compounds of this invention can also be administered in sustained release forms or from sustained release drug delivery systems. A description of representative sustained release materials can also be found in the incorporated materials in *Remington's Pharmaceutical Sciences.*

In the following the present invention shall be illustrated by means of some examples which are not construed to be viewed as limiting the scope of the invention. The compounds described herein are designated following to formula IIb and are the tautomers of the compounds of formula Ib.

The HPLC, NMR and MS data provided in the examples described below were obtained as followed: HPLC: column Waters Symmetry C8 50×4.6 mm, Conditions: a- MeCN/H$_2$O 0.09% TFA, 0 to 100% (10 min); b- MeCN/H$_2$O 0.09% TFA, 0 to 100% (20 min); c- MeCN/H$_2$O 0.09% TFA, 5 to 100% (10 min), max plot 230-400 nm; d- MeCN/H$_2$O, 5 to 100% (10 min), max plot 230-400 nm; Mass spectrum: Perkin Elmer API 150 EX (APCI); $^1$H-NMR: Brucker DPX-300 MHz.

EXAMPLES

Example 1

Preparation of 1,3-benzothiazol-2-yl(2-chloro-4-pyrimidinyl)-acetonitrile (1)

To a stirred suspension of NaH (60% in oil, 9.2 g, 0.23 mol) in dry THF (200 ml) was added drop wise under inert atmosphere a solution of 1,3-benzothiazol-2yl-acetonitrile (20 g, 0.15 mol) in dry THF (200 ml). After 1 h30 stirring at r.t., a solution of 2,4-dichloropyrimidine (17.1 g, 0.15 mol) in dry THF (200 ml) was added dropwise. The reaction mixture was allowed to stir under inert atmosphere at r.t. until complete disappearance of the starting material. The reaction was quenched by addition of water and the THF was evaporated. Water was added and the suspension was slightly acidified with aqueous HCl 1M. The precipitate obtained was filtered off and washed thoroughly with water until neutral then with hexane to remove the oil. The crude solid was dried under vacuum at 40° C., affording 28 g (84%) of the title compound as a light brown powder: mp 246° C. dec.; MS: 286.8 (M+1); HPLC (Conditions a, 268 nm) 97%, rt.5.66 min; $^1$HNMR (DMSO-d6) δ 13.25 (br s, 1H, exchangeable), 8.09 (d, J=4.14 Hz, 1H), 7.90 (d, J=7.53 Hz, 1H), 7.61 (d, J=7.92 Hz, 1H), 7.39-7.34 (m, 1H), 7.20-7.15 (m, 1H), 6.96 (br d, 1H).

CHN analysis: C$_{13}$H$_7$ClN$_4$S: Calculated: C, 54.19%, H 2.48%, N 19.45%; Found: C 53.35%, H 2.77%, N 17.62%

Upon using the procedure described above in the example 1 and the appropriate starting material and reagents, the following additional benzothiazole derivatives of formula I could be obtained.

1,3-benzothiazol-2-yl(2,6 diethoxy-4-pyrimidinyl)acetonitrile (2)

Y=11.3%; MS: 313.0 (M+1); HPLC (Conditions b, 372 nm): 97%, rt. 13.90 min $^1$HNMR (DMSO-d6) δ 12.78 (br s, 1H, exchangeable), 7.85 (d, J=7.73 Hz, 1H, 7.55 (d, J=7.97 Hz, 1H), 7.42-7.37 (m, 1H), 7.25-7.20 (m, 1H), 6.19 (s, 1H), 4.07 (s, 3H), 3.86 (s, 3H).

1,3-benzothiazol-2-yl(2-chloro-6-methyl-4-pyrimidinyl)acetonitrile (3)

Y=42.8%; MS: 300.8 (M+1); HPLC (Conditions b, 254 nm): 92%; rt. 13.91 min.

$^1$HNMR (DMSO-d6) δ13.22 (br s, 1H, exchangeable), 7.96 (d, J=7.79 Hz, 1H), 7.63 (d, J=8.17 Hz, 1H), 7.48-7.42 (m, 1H), 7.30-7.25 (m, 1H), 7.07 (s, 1H), 2.39 (s, 3H).

1,3-benzothiazol-2-yl[2-(methylsulfanyl)-4-pyrimidinyl]acetonitrile (4)

Y=73.5%; MS: 298.8 (M+1); HPLC (Conditions a, 254 nm): 99%, rt. 4.64 min $^1$HNMR (DMSO-d6) δ 13.01 (br s, 1H, exchangeable), 8.10 (br d, 1H), 7.93 (d, J=7.75 Hz, 1H), 7.66 (d, J=8.01 Hz, 1H), 7.45-7.40 (m, 1H), 7.29-7.23 (m, 1H), 6.84 (br d, 1H), 2.71 (s, 3H).

1,3-benzothiazol-2-yl(6-chloro-5-nitro-4-pyrimidinyl)acetonitrile (5)

Y=7.3%; MS: 332.0 (M+1); HPLC (Conditions a, 270 nm): 86%, rt. 6.10 min

¹HNMR (DMSO-d6) δ 8.80 (s, 1H), 8.00 (d, J=7.91 Hz, 1H), 7.77 (d, J=8.29 Hz, 1H), 7.53-7.47 (m, 1H), 7.38-7.32 (m, 1H).

1,3-benzothiazol-2-yl(2-hydroxy-pyrimidin-4-yl)acetonitrile (6)

Y=36.2%; MS: 269.0 (M+1); HPLC (Conditions a, 271 mm): 90%, rt 525 min

¹HNMR (DMSO-d6) δ 12.86 (br s, 1H, exchangeable), 11.82 (br s, 1H, exchangeable), 8.06 (d, J=8 Hz, 1H), 7.89 (d, J=8.04 Hz, 1H), 7.58 (d, J=7.28 Hz, 1H), 7.53-7.48 (m, 1H), 7.40-7.35 (m, 1H), 6.11 (d, J=7.31 Hz, 1H).

(2-chloropyrimidin-4-yl)[5-(trifluoromethyl)-1,3-benzothiazol-2-yl]acetonitrile (8)

Y=58.6%; MS: 352.6 (M−1); HPLC (Conditions c, max plot): 99.8%, rt. 5.96 min

¹H NMR (DMSO-d6) δ 8.37 (d, J=5.66 Hz, 1H), 8.21 (d, J=8.29 Hz, 1H), 7.87 (s, 1H), 7.60 (d, J=7.91 Hz, 1H), 7.23-7.19 (m, 1H).

(2-chloro-4-pyrimidinyl)(3-methyl-1,3-benzothiazol-2(3H)-ylidene)ethanenitrile (9)

To a solution of 1 (0.1 g, 0.35 mmol) in dry DMSO was added dry $K_2CO_3$ then methyl iodide and the suspension was shaken at rt. for 2 days. The precipitate formed by addition of water was filtered off then washed with water until neutral pH. The crude residue, dried under vacuum at 40° C., was triturated in warm acetonitrile, filtered off then dried under vacuum at 40° C., affording 5.6 mg (5%) of the title compound as a yellow powder.

MS: 623 (2M+Na); HPLC (Conditions a, 388 nm): 99%, rt. 5.31 min

¹HNMR (DMSOd-6): δ 8.01 (d, J=7.7 Hz, 1H), 7.83 (d, J=8.0 Hz, 1H), 7.79 (d, J=7.4 Hz, 1H), 7.45-7.40 (m, 1H), 7.31-7.24 (m, 1H), 6.81 (d, J=7.4 Hz, 1H), 3.67 (s, 3H)

Example 2

Preparation of 1,3-benzothiazol-2-yl(2-{[2-(1H-imidazolyl-4-yl)ethyl]amino}-4-pyrimidinyl)acetonitrile (10)

To a suspension of 1 (0.1 g, 0.35 mmol) in dry EtOH (3 ml) was added Et₃N (0.05 ml, 0.35 mmol) and histamine (0.078 g, 0.70 mmol). After sonication, the yellow solution was shaken at 70° C. for 3 days. The yellow precipitate formed was filtered off and washed with H2O (2×) then EtOH (3×) and dried under vacuum at 40° C., affording 47 mg (37%) of the title compound as a bright yellow powder. mp 257-258° C., 10 was taken up in a mixture of DCM/TFA. The yellow fluffy solid formed by addition of ether was filtered off, washed with ether (3×) then dried under vacuum at 40° C., affording 36 mg (29%) of the title compound as a yellow powder: mp 247-249° C., MS: 362.0 (M+1); HPLC (Conditions a, 265 nm): 98%, rt. 2.87 min; ¹H NMR (DMSO-d6): δ 14.25 (br s, 2H, exchangeable), 11.05 (br s, 1H, exchangeable), 9.03 (s, 1H), 7.94-7.87 (m, 1H), 7.74-7.71 (m, 2H), 7.57-7.52 (m; 2H),7.42-7.37 (m, 1H), 7.24-7.19 (m, 1H), 6.40 (d, J=7.1 Hz, 1H), 3.97-3.55 (m, 3H), 3.11-3.05 (m, 2H).

CHN analysis: C18H15N7S. 2TFA: Calculated: C 44.83%, H 2.91%, N 16.63%; Found: C 44.59%, H 3.18%, N 16.43%

Upon using the procedure described above in the example 2 and the appropriate starting material and reagents, the following additional benzothiazole derivatives of formula II could be obtained.

1,3-benzothiazol-2-yl[2-(1-piperazinyl)-4-pyrimidinyl]acetonitrile (2 TFA) (11)

Y=37%; MS: 337.2 (M+1); HPLC (Conditions a, 271 nm): 96%, rt. 2.58 min

¹H NMR (DMSO-d6): δ 9.13 (br s, 2H, exchangeable), 7.96 (br d, 1H), 7.90 (d, J=7.74 Hz, 1H), 7.65 (d, J=8.0 Hz, 1H), 7.45-7.40 (m, 1H), 7.29-7.24 (m, 1H), 6.58 (d, J=6.0 Hz, 1H), 4.70-3.60 (m, 5H), 3.38-3.20 (m, 4H).

1,3-benzothiazol-2-yl[2-(4-benzyl-1-piperidinyl)-4-pyrimidinyl]acetonitrile (TFA ) (12)

Y=52%; MS: 426.0 (M+1); HPLC (Conditions a, 394 nm): 99%, rt. 5.42 min

¹H NM DMSO-d6): δ 7.94 (d, J=7.78 Hz, 1H), 7.72-7.69 (m, 2H), 7.46-7.41 (m, 1H), 7.32-7.24 (m, 3H), 7.21-7.18 (m, 3H), 6.50 (d, J=6.2 Hz, 1H), 4.55-4.51 (m, 2H), 4.35-3.45 (m, 1H), 3.16-3.04 (m, 2H), 2.56 (d, J=7.0 Hz, 2H), 2.00-1.85 (m, 1H), 1.81-1.72 (m, 2H), 1.34-1.21 (m, 2H).

1,3-benzothiazol-2-yl[2-(4-methyl-1-piperazinyl)-4-pyrimidinyl]acetonitrile (2 TFA) (13)

Y=30%; MS: 351.0 (M+1); HPLC (Conditions a, 271 nm): 99%, rt. 2.54 min

¹H NMR (DMSO-d6): δ 10.10 (br s, 2H, exchangeable), 8.05 (br d, 1H), 7.88 (d, J=7.8 Hz, 1H), 7.63 (d, J=8.0 Hz, 1H), 7.45-7.40 (m, 1H), 7.29-7.24 (m, 1H), 6.60 (d, J=5.8 Hz, 1H), 4.95-4.70 (m, 2H), 4.42-3.68 (m, 1H), 3.67-3.50 (m, 2H), 3.48-3.31 (m, 2H), 3.26-3.05 (m, 2H, 2.86 (s, 3H).

1,3-benzothiazol-2-yl[2-4-morpholinyl)-4-pyrimidinyl]acetonitrile (TFA) (14)

Y=55%; MS: 338.0 (M+1); HPLC (Conditions a, 270 nm): 99%, rt. 3.51 min

¹H NMR (DMSO-d6): δ7.94 (d, J=7.8 Hz, 1H), 7.79 (br d, 1H), 7.70 (d, J=8.0 Hz, 1H), 7.45-7.40 (m, 1H), 7.30-7.25 (m, 1H), 6.54 (d, J=6.3 Hz, 1H), 4.40-3.65 (m, 9H)

1,3-benzothiazol-2-yl[2-(methylamino)-4-pyrimidinyl]acetonitrile (TFA salt) (15)

Y=11%; MS: 282.0 (M+1); HPLC (Conditions a, 270 nm): 97%, rt. 3.39 min

¹H NMR (DMSO-d6): δ11.70 (v br s, 1H, exchangeable) 8.15-7.90 (m, 2H [1+1 exchangeable]), 7.85-7.55 (m, 2H), 7.46-7.41 (m, M1H), 7.30-7.25 (m, 1H), 6.43 (d, J=6.0 Hz, 1H), 4.81-3.78 (m, 1H), 3.10 (s, 3H)

1,3-benzothiazol-2-yl(2-{4[2-(4-morpholinyl)ethyl]-1-piperazinyl}-4-pyrimidinyl)-acetonitrile (3 TFA) (16)

Y=78%; MS: 450.2 (M+1); HPLC (Conditions a, 270 nm): 99%, rt. 2.67 min

¹HNMR (DMSO-d6) δ7.91 (br d, 1H), 7.86 (d, J=7.73 Hz, 1H), 7.66 (d, J=8.01 Hz, 1H), 7.45-7.40 (m, 1H), 7.29-7.24

(m, 1H), 6.56 (d, J=5.94 Hz, 1H), 4.10-3.93 (m, 4H), 3.85-3.42 (m, 5H), 3.32-3.23 (m, 4H), 3.18-3.04 (m, 8H)

1,3-benzothiazol-2-yl{2-[4-(benzyloxy)-1-piperidinyl]-4-pyrimidinyl}acetonitrile (TFA) (17)

Y=76.2%; MS: 442.2 (M+1); HPLC (Conditions a, 268 nm): 99%, rt. 5.00 min $^1$HNMR (DMSO-d6): δ 7.92 (d, J=7.94 Hz, 1H), 7.70 (d, J=8.08 Hz, 1H), 7.65 (br d, 1H), 7.43-7.35 (m, 5H), 7.32-7.22 (m, 2H), 6.46 (d, J=6.6 Hz, 1H), 4.59 (s, 2H), 4.20-4.06 (m, 2H), 3.81-3.72 (m, 1H), 3.70-3.59 (m, 2H), 3.57-3.20 (m, 1H), 2.09-1.96 (m, 2H), 1.77-1.61 (m, 2H)

1,3-benzothiazol-2-yl[2-(4-hydroxy-1-piperidinyl)-4-pyrimidinyl]acetonitrile (TFA) (18)

Y=14%; MS: 352 (M+1); HPLC (Conditions a, 271 nm): 97%, rt. 3.21 min $^1$HNMR (DMSO-d6): δ7.95 (d, J=7.79 Hz, 1H), 7.72-7.65 (m, 2H), 7.45-7.40 (m, 1H), 7.28-7.23 (m, 1H), 6.48 (, d, J=6.07 Hz, 1H), 4.60-3.75 (m, 5H), 3.58-3.51 (m, 2H), 1.95-1.82 (m, 2H), 1.55-1.42 (m, 2H)

1,3-benzothiazol-2-yl(2-hydrazino-4-pyrimidinyl)acetonitrile (TFA) (19)

Y=60%; MS: 283.0 (M+1); HPLC (271 nm): 98%, rt. 3.17 min $^1$HNMR (DMSO-d6): δ 9.78 (br s, 1H, exchangeable), 7.89-7.75 (m, 4H), 7.48-7.43 (m, 1H), 7.32-7.27 (m, 1H), 6.53 (br d, 1H), 4.25-3.40 (m, 1H).

1,3-benzothiazol-2-yl(2-{[2-(dimethylamino)ethyl]amino}-4-pyrimidinyl)acetonitrile (2 TFA) (20)

Y=30%; MS: 339.0 (M+1); HPLC (Conditions a, 270 nrm): 99%, rt. 2.69 min $^1$H NMR (DMSO-d6): δ 11.85 (v br s, 1H, exchangeable), 9.59(br s, 1H), 7.90 (br d,2H), 7.73 (d, J=7.9 Hz, 1H), 7.60 (br d, 1H), 7.43-7.38 (m, 1H), 7.27-7.22 (m, 1H), 6.43 (d, J=6.8 Hz, 1H), 4.25-3.70 (m, 3H), 3.51-3.41 (m, 2H), 2.87 (s, 6H).

1,3-benzothiazol-2-yl[2-(dimethylamino)-4-pyrimidinyl]acetonitrile (21)

Y=12%; MS: 295.8 (M+1); HPLC (Conditions a, 270 nim): 99%, rt. 3.50 min $^1$H NMR (DMSO-d6):δ 11.20,(br s, 1H), 7.88 (d, J=7.76 Hz 1H1), 7.69 (d, J'8 Hz 1H), 7.46 (br d, 1H), 7.38-7.33 (m, 1H), 7.20-7.16 (m, 1H), 6.38 (d, J=6.9 Hz, 1H), 3.26 (s, 6H).

1,3-benzothiazol-2-yl{2-[(2-methoxyethyl)amino]-4-pyrimidinyl}acetonitrile (22)

Y=54%; MS: 326.0 (M+1); HPLC (Conditions a, 273 nm): 99%, rt. 3.66 min

1HNMR (DMSO-d6): δ10.83 (s, 1H, 7.85 (d, J=7.54 Hz, 1H), 7.72 (d, J=7.91 Hz, 1H), 7.60 (br s, 1H), 7.44 (d, J=6.78 Hz, 1H, 7.38-7.33 (m, 1H), 7.22-7.16 (m, 1H), 6.33 (d, J=7.16 Hz, 1H), 3.82-3.74 (m, 2H), 3.62 (t, J=5.27 Hz, 2H), 3.31 (s, 3H)

1,3-benzothiazol-2-yl{2-[(2-hydroxyethyl)amino]-4-pyrimidinyl}acetonitrile (23)

Y=80%; MS: 312.2 (M+1); HPLC (Conditions a, 273 nm): 99%, rt. 3.16 min $^1$HNMR (DMSOd6): δ 10.85 (s, 1H), 7.86 (d, J=7.91 Hz, 1H), 7.71 (d, J=7.91 Hz, 1H), 7.57 (br s, 1H), 7.44 (d, J=7.16 Hz, 1H), 7.38-7.32 (m, 1H), 7.21-7.16 (m, 1H), 6.32 (d, J=7.16 Hz, 1H), 4.92 (br s, 1H), 3.68 (br s, 4H)

1,3-benzothiazol-2-yl[2(propylamino)-4-pyrmidinyl]acetonitrile (24)

Y=81%; MS: 310.0 (M+1); HPLC (Conditions a, 273 nm): 95%, 4.04 min $^1$HNMR (DMSO-d6): δ10.91 (br s, 1H), 7.84 (d, J=7.54 Hz, 1H), 7.71 (d, J=8.29 Hz, 1H), 7.62 (br s, 1H), 7.42 (d, J=6.78 Hz, 1H), 7.38-7.32 (m, 1H), 7.21-7.16 (m, 1H), 6.31 (d, J=7.53 Hz, 1H), 3.42-3.33 (m, 2H), 1.71-1.64 (m, 2H), 1.02-0.97 (m, 3H)

1,3-benzothiazol-2-yl(2-{[3-(1H-imidazol-1-yl)propyl]amino}-4-pyrimidinyl)acetonitrile (TFA) (25)

Y=57%, MS: 376.0 (M+1); HPLC (Conditions a, 270 nm): 98%, rt. 2.80 min $^1$H NMR DMSO-d6): δ 14.40 (br s, 1 H, exchangeable), 11.60 (br s, 1 H, exchangeable), 9.18 (s, 1H), 8.13 (br d, 1H), 7.92-7.85 (m, 2H), 7.74-7.59 (m, 3H), 7.43-7.39 (m, 2H), 7.28-7.23 (m, 1H), 6.40 (d, J=7.2 Hz, 1H), 4.35 (t, J=6.8 Hz, 2H), 3.70-3.45 (m, 2H), 5.05-4.20 (m, 1H), 2.35-2.10 (m, 2H)

1,3-benzothiazol-2-yl[2-(1-pyrrolidinyl)-4-pyrimidinyl]acetonitrile (26)

Y=27%, mp=270-272° C., MS: 322.0 (M+1); HPLC (Conditions a, 372 nm): 98%, rt. 3.90 min $^1$H NMR (DMSO-d6):δ 11.30 (v br s, 1 H, exchangeable), 7.86 (d, J=7.2 Hz, 1H), 7.66 (d, J=7.9 Hz, 1H), 7.46 (d, J=6.8 Hz, 1H), 7.35-7.30 (m, 1H), 7.17-7.12 (m, 1H), 6.33 (d, J=6.8 Hz, 1H), 3.90-3.45 (m, 4H), 2.08-1.94 (m, 4H).

1,3-benzothiazol-2-yl {2-[(2-phenylethyl)amino]-4-pyrimidinyl}acetonitrile (27)

Y=46.1%; mp=256° C. dec., MS: 371.8 (M+1); HPLC (Conditions a, 270 nm): 99%, rt. 4.64 min $^1$HNMR (DMSO-d6): δ11.04 (br s, 1H), 7.71 (d, J=8.29 Hz, 1H), 7.64-7.61 (m, 2H), 7.45 (d, J=7.16 Hz, 1H), 7.37-7.32 (m, 5H), 7.29-7.26 (m, 1H), 7.20-7.16 (m, 1H), 6.33 (d, J=7.17 Hz, 1H), 3.94-3.81 (m, 2H), 2.99 (t, J=7.54 Hz, 2H)

1,3-benzothiazol-2-yl(2-{[2-(2-pyridinyl)ethyl]amino}-4-pyrimidinyl)acetonitrile (2 TFA) (28)

Y=80%; mp=247° C. dec., MS: 373.2 (M+1); HPLC (Conditions a, 266 nm): 99%, rt. 2.85 min $^1$HNMR (DMSO-d6) δ8.70 (d, J=5.28 Hz, 1H), 8.15-8.10 (m, 1H), 7.88 (br s, 1H), 7.75-7.72 (m, 2H), 7.67 (d, J=7.91 Hz, 1H), 7.61-7.50 (m, 2H), 7.44-7.39 (m, 1H), 7.28-7.23 (m, 1H), 6.44 (d, J=7.14 Hz, 1H), 4.65-3.60 (m, 3H), 3.32-3.28 (m, 2H)

CHN analysis: $C_{20}H16N6S$. 2TFA: Calculated: C 47.29%, H 3.14%, N 13.79%; Found: C 47.47%, H 3.21%, N 13.71%

1,3-benzothiazol-2-yl{2-[(2-pyridinylmethyl)amino]-4-pyrimidinyl}acetonitrile (2 TFA) (29)

Y=52%; mp=250° C. dec., MS: 359.0 (M+1); HPLC (Conditions a, 266 nm): 99%, rt. 2.84 min ¹HNMR (DMSO-d6): δ8.66 (d, J=4.9 Hz, 1H), 8.38 (br s, 1H), 7.99-7.94 (m, 1H), 7.82 (d, J=7.91 Hz, 1H), 7.71-7.69 (m, 2H), 7.64 (d, J=7.91 Hz, 1H), 7.45-7.38 (m, 2H), 7.28-7.23 (m, 1H), 6.48 (d, J=6.78 Hz, 1H), 5.00 (br s, 2H), 5.15-4.05 (m, 2H).
CHN analysis: C19H14N6S. 2TFA: Calculated: C 47.10%, H 2.75%, N 14.33%; Found: C 46.93%, H2.96%, N 14.24%

1,3-benzothiazol-2-yl{2-[4-(1H-1,2,3-benzotdazol-1-yl)-1-piperidinyl]-4-pyrdiniyl}acetonitrile (TFA) (30)

Y=65%; MS: 453.2 (M+1); HPLC (Conditions a, 254 nm): 90%, rt. 4.39 min
¹HNMR (DMSO-d6): δ 8.06 (d, J=8.29 Hz, 1H), 8.01 (d, J=8.67 hz, 1H), 7.91 (d, J=7.91 Hz, 1H), 7.80 (br d, 1H), 7.70 (d, J=8.29 Hz, 1H), 7.60-7.55 (m, 1H), 7.44-7.39 (m, 1H), 7.27-7.22 (m, 1H), 8.01-7.22 (very br m, 1H), 6.56 (d, J=6.42 Hz, 1H), 5.40-5.33 (m, 1H), 4.79-4.74 (m, 2H), 4.90-3.90 (m, 1H), 3.57-3.50 (m, 2H), 2.37-2.27 (m, 4H)

1,3-benzothiazol-2-yl{2-[4-(2-pyrazinyl)-1-piperazinyl]pyrimidinyl}acetonitrile (TFA) (31)

Y=88%; MS: 415.2 (M+1); HPLC (Conditions a, 254 nm): 99%, rt. 3.74 min
¹HNMR(DMSO-d6): δ 8.39 (br d, 1H), 8.13 (dd, J=2.64, 1.51 Hz, 1H), 7.97 (d, J=7.91 Hz, 1H), 7.88 (d, J=2.63 Hz, 1H), 7.79 (br d, 1H), 7.71 (d, J=7.91 Hz, 1H), 7.46-7.41 (m, 1H), 7.31-726 (m, 1H), 8.13-7.26 (v br m, 1H), 6.53 (d, J=6.78 Hz, 1H), 4.06-3.96 (m, 4H), 3.87-3.77 (m, 4H), 4.60-3.65 (m, 1H)

1,3-benzothiazol-2-yl{2-[4(2-pyrimidinyl)-1-piperazinyl]-4-pyrimidinyl}acetonitrile (TFA) (32)

Y=85%; MS: 415.2 (M+1); HPLC (Conditions a, 254 rum): 99%, rt. 3.81 min
¹HNMR (DMSO-d6): δ 8.44 (d, J=4.52 Hz, 2H), 8.03 (d, J=7.91 Hz, 1H), 7.83 (br d, 1H), 7.78 (d, J=7.91 Hz, 1H), 7.48-7.43 (m, 1H), 7.32-7.27 (m, 1H), 8.44-7.27 (very br m, 1H), 6.71-6.68 (m, 1H), 6.56 (d, J=6.4 Hz, 1H), 5.15-4.10 (m, 1H), 3.98 (s, 8H)

1,3-benzothiazol-2-yl(2-{[2-(3-pyridinyl)ethyl]amino}-4-pyrimidinyl)acetonitrile (2 TFA) (33)

Y=74%; MS: 373.0 (M+1); HPLC (Conditions a, 263 nm): 99%, rt. 2.92 min
¹HNMR (DMSO-d6): δ8.81 (d, J=1.13 Hz, 1H), 8.71 (dd, J=5.27 Hz, J=1.13 Hz, 1H), 8.31 (d, J=7.91 Hz, 1H), 7.94 (br s, 1H), 7.85-7.73 (m, 3H), 7.60 (br d, 1H), 7.45-7.40 (m, 1H), 7.29-7.24 (m, 1H), 6.43 (d, J=7.14 Hz, 1H), 6.00-4.40 (m, 2H), 4.05-3.87 (m, 2H), 3.19-3.15 (m, 2H)

1,3-benzothiazol-2-yl(5-bromo-2-{[2-(dimethylamino)ethyl]amino}-4-pyrimidinyl)-acetonitrile (34)

Y=2%; MS: 419.0 (M+1); HPLC (Conditions a, 285 nm): 88%, rt. 8.00 min
¹H NMR (DMSO-d6): δ 11.30 (v br s, 1 H, exchangeable), 7.76 (s, 1H), 7.67 (d, J=7.6 Hz, 1H), 7.51 (d, J=7.8 Hz, 1H), 7.26-7.21 (m, 1H), 7.04-6.99 (m, 1H), 6.55 (br s, 1H), 3.75-3.45 (m, 2H), 3.15-2.95 (m, 2H), 2.64 (s, 6H).

1,3-benzothiazol-2-yl{2-[(2-morpholin-4-ylethyl)amino]pyrimidin-4-yl}acetonitrile (di TFA) (35)

Y=53%; MS: 381.0 (M+1); HPLC (Conditions a, 254 nm): 99.5%, rt. 2.80 min
¹H NMR (DMSO-d6): δ 10.9 (v br s, 1 H, exchangeable), 8.00-7.98 (m, 2H), 7.73 (d, J=7.9 Hz, 1H), 7.58 (br s, 1H), 7.42-7.37 (m, 1H), 7.27-7.22 (m, 1H), 6.55 (d, J=7.15 Hz, 1H), 4.24-3.18 (m, 12H).
¹H NMR (D20): δ 7.59 (d, J=7.9 Hz, 1M, 7.39-7.29 (m, 2H), 7.20-7.15 (m, 2H), 6.20 (d, J=6.8 Hz, 1H), 3.89-3.82 (m, 6H), 3.45-3.32 (m, 6H)

1,3-benzothiazol-2-yl[2-(4-{3-[(trifluoromethyl)sulfonyl]anilino}piperidin-1-yl)pyrimidin-4-yl]acetonitrile (TFA) (36)

Y=69%; MS: 559.2 (M+1); HPLC (Conditions a, 254 nm): 96%, rt. 5.60 min
¹H NMR (DMSO-d6): δ 7.94 (d, J=7.54 Hz, 1H), 7.61-7.59 (m, 2H), 7.56-7.49 (m 1H), 7.45-7.38 (m, 1H), 7.27-7.16 (m, 4H), 6.72-6.59 (v br s, 1H), 6.51-6.48 (br s, 1H), 4.50-3.40 (in 5H), 2.13-2.08 (m, 2H), 1.52-1.48 (m, 2H).

1,3-benzothiazol-2-yl(2-{[3-(2-oxopyrrolidin-1-yl)propyl]amino}pyrimidin-4-yl)acetonitrile (TFA) (37)

Y=65%; MS: 3.93.0 (M+1); HPLC (Conditions a, 254 nm): 98%, rt. 3.52 min
¹H NMR (DMSO-d6): δ 11.50 (v br s, 1H, exchangeable), 8.15-8.02 (br s, 1H), 7.95-7.60 (m, 4H), 7.46-7.41 (m, 1H), 7.31-7.25 (m, 1H), 6.45 (br s, 1H), 3.70-3.50 (m, 2H), 3.48-2.28 (m, 4H), 2.23-2.17 (m, 2H), 1.92-1.84 (m, 4H).
CHN analysis: C20H20N6O1S Calculated: C, 51.80%, H 4.23%, N 16.47%; Found: C 51.59%, H 4.26%, N 16.16%

1,3-benzothiazol-2-yl(2-{methyl[3-(methylamino)propyl]amino}pyrimidin-4-yl)acetonitrile (di TFA) (38)

Y=11%; MS: 353.2 (M+1); HPLC (Conditions a, 272 nm): 96%, rt. 2.88 min
¹H NMR (DUMSO-d6): δ 11.30 (v br s, 1H, exchangeable), 8.50-8.25 (br s,2H), 7.92 (d, J'7.91 Hz, 1H), 7.72-7.68 (m, 2H), 7.43-7.37 (m, 1H), 7.27-7.21 (m, 1H), 6.46 (d, J=6.8 Hz, 1H), 4.00-3.65 (m, 2H), 3.22 (s, 3H), 3.10-2.85 (m, 2H), 2.63-2.51 (m, 3H), 2.10-1.80 (m, 2H).

1,3-benzothiazol-2-yl(2-{[3-(4-methylpiperazin-1-yl)propyl]amino}pyrimidin-4-yl)acetonitrile (tri TFA salt) (39)

Y=65.2%; MS: 408.0 (M+1); HPLC (Conditions a, 272 nm): 99.2%, rt. 2.67 min
¹H NMR DMSO-d6) δ 7.94-7.91 (m, 2H), 7.74 (d, J=7.92 Hz, 1H), 7.56 (br d, 1H), 7.43-7.38 (m, 1H), 7.27-7.22 (m, 1H), 6.40 (d, J=7.17 Hz, 1H), 4.95-4.05 (m, 1H), 3.71-3.60 (m, 2H, 3.54-3.15 (m, 4H), 3.02-2.86 (m, 4H), 2.75 (s, 3H), 2.03-1.91 (m, 2H).

1,3-benzothiazol-2-yl{2-[(3-morpholin-4-ylpropyl)amino]pyrimidin-4-yl}acetonitrile (di TFA salt) (40)

Y=73.9%; MS: 408.2 (M+1); HPLC (Conditions a, 272 nm): 99.6%, rt 2.77 min

¹H NMR (DMSO-d6) δ 9.66 (br s, 1H), 7.94 (d, J=7.91 Hz, 1H), 7.86 (br s, 1H) 7.73 (d, J=7.91 Hz, 1H) 7.55 (br d, 1H), 7.43-7.38 (m, 1H),7.27-7.22 (m, 1H), 6.40 (d, J=7.17 Hz, 1H), 4.15-3.52 (m, 7H[6+1]), 3.49-3.38 (m, 2H), 3.29-3.19 (m, 2H), 3.16-3.00 (m, 2H), 2.15-2.01 (m, 2H).

1,3-benzothiazol-2-yl(2-{[2-(1-methyl-1H-imidazol-4-yl)ethyl]amino}pyrimidin-4-yl)acetonitrile (41)

Y=58.8%; MS: 376.0 (M+1); HPLC (Conditions a, 272 nm): 99.3%, rt. 3.09 min
¹H NMR (DMSO-d6) δ 11.20 (very br s, 1H), 9.00 (s, 1H), 7.90 (br s, 1H), 7.78-7.72 (m, 2H), 7.58-7.54 (m, 2H), 7.43-7.38 (m, 1H), 7.27-7.22 (m, 1H), 6.41 (d, J=7.17 Hz, 1H), 4.60-4.10 (m, 1H), 3.93-3.85 (m, 2H), 3.83 (s, 3H), 3.11-3.02 (m, 2H).

1,3-benzothiazol-2-yl(2-{[2-(1H-indol-3-yl)ethyl]amino}pyrimidin-4-yl)acetonitrile (42)

Y=60.6%; MS: 411.0 (M+1); HPLC (Conditions a, 272 nm): 99.9%, rt. 4.94 min
¹H NMR (DMSO-d6) δ 11.25 (very br s, 1H), 10.98 (s, 1H),7.92-7.79 (m, 1H),7.71 (d, J=7.92 Hz, 1H), 7.63-7.57 (m, 2H), 7.42-7.37 (m, 3H), 7.28 (br d, 1H), 7.21-7.16 (m, 1H), 7.10-7.05 (m, 1H), 6.97-6.92 (m, 1H), 6.44 (d, J=m7.17 Hz, 1H), 4.60-3.70 (m, 3H[2+1]), 3.12 (t, J=7.15 Hz, 2H).

1,3-benzothiazol-2-yl(2-{[2-(4-hydroxyphenyl)ethyl]amino}pyrimidin-4-yl)acetonitrile (43)

Y=76%; m.p. 258-261° C.; MS: 388.0 (M+1); HPLC (Conditions a, 272 nm): 98.8%, rt. 4.00 min
¹H NMR (DMSO-d6) δ 9.25 (br s, 1H), 7.75-7.69 (m, 2H), 7.59 (br d, 1H), 7.45-7.40 (m, 1H), 7.29-7.24 (m, 1H), 7.12 (d, J=8.29 Hz, 1H), 6.74 (d, J=8.29 Hz, 1H) 6.43 (d, J=6.78 Hz, 1H), 3.89-3.71 (m, 2H), 2.90-2.85 (m, 2H)

Tert-butyl ({4-[1,3-benzothiazol-2-yl(cyano)methyl]pyrimidin-2-yl}amino)acetate (TFA salt) (44)

Y=72%; MS: 382.0 (M+1); HPLC (Conditions a, 272 mn): 98.2%, rt. 4.37 min
¹H NMR (DMSO-d6) δ 11.30 (v br s, 1H, exchangeable), 7.92 (br s, 1H, exchangeable), 7.82 (d, J=7.54 Hz, 1H), ), 7.75 (d, J=8.23 Hz, 1H), 7.61 (br d, 1H), 7.46-7.39 (m, 1H), 7.32-7.26 (m, 1H), 6.45 (d, J=6.78 Hz, 1H), 4.50-3.80 (m, 2H), 1.40 (s, 9H)

{2-[(3-aminopropyl)amino]pyrimidin-4-yl}(1,3-benzothiazol-2-yl)acetonitrile (di TFA) (45)

Y=62%; MS: 325.0 (M+1); HPLC (Conditions a, 382 nm): 90.0%, rt. 2.67 min
¹H NMR (DMSO-d6) δ 11.60 (v br s, 1H, exchangeable), 7.99 (br s, 1H, exchangeable), 7.90 (d, J=7.92 Hz, 1H), 7.75-7.49 (m, 3H), 7.44-7.37 (m, 1H), 7.27-7.22 (m, 1H), 6.39 (d, J=7.16 Hz, 1H, 5.50-4.00 (m, 3H, exchangeable), 3.80-3.5 (m, 2H), 3.00-2.80 (m, 2H), 2.10-1.80 (m, 2H).

{2-[(2-aminoethyl)amino]pyrimidin-4-yl}(1,3-benzothiazol-2-yl)acetonitrile (di TFA) (46)

Y=86%; MS: 311.0 (M+1); HPLC (Conditions a, 382 in): 95%, rt. 2.64 min
¹H NMR (DMSO-d6) δ 11.60 (v br s, 1H, exchangeable), 7.95-7.86 (m, 3H), 7.73 (d, J=7.91 Hz, 1H), 7.59 (br d, 1H), 7.43-7.37 (m, 1H), 7.28-7.22 (m, 1H), 6.43 (d, J=7.16 Hz), 1H), 5.50-4.00 (m, 3H, exchangeable), 3.90-3.70 (m, 2H), 3.25-3.10 (m, 2H).

1,3-benzothiazol-2-yl(2-{[3-(dimethylamino)propyl]amino}pyrimidin-4-yl)acetonitrile (di TFA salt) (47)

Y=54%; mp. 204-205° C.; MS: 353.0 (M+1); HPLC (Conditions a, 272 nm): 98%, rt. 2.75 min
¹H NMR (DMSO-d6) δ 11.4 (v br s, 1H), 9.43 (s, 1H), 7.94 (d, J 7.91 Hz, 1H). 7.90 (br s, 1H), 7.73 (d, J=7.91 Hz, 1H), 7.55 (br d, 1H), 7.43-7.37 (m, 1H), 7.27-7.22 (m, 1H), 6.39 (d, J=7.14 Hz, 1H), 4.80-4.00 (m, 1H), 3.71-3.60 (m, 2H), 3.24-3.13 (m, 2H), 2.78 (d, J=4.14 Hz, 6H), 2.11-1.99 (m, 2H)

1,3-benzothiazol-2-yl{2-[(2-piperidin-1-ylethyl)amino]pyrimidin-4-yl}acetonitrile (di TFA salt) (48)

Y=12%; mp. 228-230° C.; MS: 379.0 (M+1); HPLC (Conditions a, 270 nm): 99.9%, rt. 2.84 min
¹H NMR (DMSO-d6) δ 9.18 (br s, 1H), 7.89-7.87 (m, 2H), 7.74 (d, J=7.91 Hz, 1H), 7.62 (br s, 1H), 7.44-7.39 (m, 1H), 7.29-7.24 (m, 1H), 6.45 (d, J=7.17 Hz, 1H), 5.25-4.30 (m, 1H), 4.05-3.93 (m, 2H), 3.63-3.50 (m, 2H), 3.48-3.37 (m, 2H), 3.07-2.92 (m, 2H), 1.90-1.30 (m, 6H)

1,3-benzothiazol-2-yl(2-{[2-(1-methyl-1H-imidazol-5-yl)ethyl]amino}pyrimidin-4-yl)acetonitrile (di TFA salt) (49)

Y=46%; m.p. 219-220° C.; MS: 376.0 (M+1); HPLC (Conditions a, 270 nm) 99.8%, rt. 2.73 mi
¹H NMR (DMSO-d6) δ 14.15 (br s, 1H), 9.03 (s, 1H), 7.83 (br s, 1H), 7.74-7.64 (m, 3H), 7.54 (br d, 1H), 7.41-7.36 (m, 1H), 7.24-7.18 (m, 1H), 6.41 (d, J=7.14 Hz, 1H), 4.50-3.88 (m, 3H), 3.78 (s, 3H), 3.10-3.05 (n, 2H)

1,3-benzothiazol-2-yl[2-(benzylamino)pyrimidin-4-yl]acetonitrile (50)

Y=78%; MS: 358.0 (M+1); HPLC (Conditions a, 254 nm): 99.2%, rt. 4.40 min
¹H NMR (DMSO-d6) δ 8.30 (br t, 1H), 7.84 (d, J=7.53 Hz, 1H), 7.71 (d, J=7.91 Hz, 1H), 7.65 (br d, 1H), 7.46-7.34 (m, 5H), 7.28-7.22 (m, 2H), 6.47 (d, J=7.14 Hz, 1H), 5.2-4.5 (m, 1H), 4.86 (br d, 2H).

Isopropyl 3-({4-[1,3-benzothiazol-2-yl(cyano)methyl]pyrimidin-2-yl}amino)propanoate (51)

Y=5%; MS: 382.0 (M+1); HPLC (Conditions a, 254 rm): 98%, rt. 5.66 min
¹H NMR (DMSO-d6) δ 8.56 (br d, 1H), 7.97 (d, J=7.16 Hz, 1H), 7.91 (d, J=6.40 Hz, 1H), 7.81 (d, J=7.91 Hz, 1H), 7.46-7.40 (m, 1H), 7.33-7.26 (m, 1H), 5.03-4.94 (m, 1H), 4.68-4.64 (m, 2H, 4.10-4.03 (m, 2H), 1.29 (d, J=6.40 Hz, 6H).

1,3-benzothiazol-2-yl{2-[(3-hydroxypropyl)amino]pyrimidin-4-yl}acetonitrile (52)

Y=44%; MS: 326.0 (M+1); HPLC (Conditions c, max plot): 99%, rt. 3.26 min
¹H NMR (DMSO-d6) δ 10.81 (br s, 1H, exchangeable), 7.84 (d, J=7.54 Hz, 1), 7.71 (d J=8.29 Hz, 1H), 7.49 (br s, 1H, exchangeable), 7.43-7.32 (m, 2, 7.21-7.15 (m, 1H), 6.32

(d, J=7.20 Hz, 1H), 4.65-4.50 (br s, 1H, exchangeable), 3.80-3.50 (m, 4H), 1.90-170 (m, 2H)

1,3-benzothiazol-2-yl{2-[(pyridin-3-ylmethyl) amino]pyrimidin-4-yl}acetonitrile (di TFA salt) (53)

Y=46%; MS: 359.0 (M+1); HPLC (Conditions c, max plot): 99.7%, rt. 2.56 min
$^1$H NMR (DMSO-d6) δ 8.87 (s, 1H), 8.64 (d, J=4.9 Hz, 1H), 8.29-8.26 (m, 2H), 7.84-7.63 (m, 4H, 7.41-7.36 (m, 1H), 7.25-7.20 (m, 1H), 6.46 (d, J=7.16 Hz, 1H), 4.97 (br d, 2H).

(2-aminopyrimidin-4-yl)(1,3-benzothiazol-2-yl)acetonitrile (54)

A suspension of 1 (0.1 g, 0.35 mmol) in a 2M solution of ammonia in ethanol (10 ml) was heated up to 150° C. in a Parr vessel for 3 h. The solution was cooled down to r.t. and the yellow precipitate formed was filtered off then washed thoroughly with ethanol/water 1:1 and water. The precipitate was dried in vacuum at 40° C. affording 48 mg (51%) of the title compound as a yellow powder.
MS: 268.0 (M+1); HPLC (Conditions c, max plot): 95%, r.t. 3.20 min
$^1$H NMR (DMSO-d6) δ 10.92 (br s, 1H, exchangeable), 7.79 (d, J=7.16 Hz, 1H), 7.70 (d, J=7.01 Hz, 1H), 7.42-7.15 (m, 5), 6.34 (d, J=7.54 Hz, 1H)

1,3-benzothiazol-2-yl{2-[(pyridin-4-ylmethyl) amino]pyrimidin-4-yl}acetonitrile (di TFA salt) (55)

Y=46.5%; MS: 359.0 (M+1); HPLC (Conditions c, max plot) 99%, rt. 2.55 min
$^1$H NMR (DMSO-d6) δ 8.77 (d, J=6.4 Hz, 1H), 8.33 (br t, 1H), 7.95-7.93 (br d, 2H), 7.79 (d, J=7.54 Hz, 1H), 7.69-7.62 (m, 2H, 7.39-7.34 (m, 1H), 7.24-7.19 (m, 1H), 6.43 (d, J=7.17 Hz, 1H), 5.05 (br d, 2H), 5.6-4.4 (br s, 1H).

tert-butyl 4-[2-({4-[1,3-benzothiazol-2-yl(cyano) methyl]pyrimidin-2-yl}amino)ethyl]-phenylcarbamate (56)

Y=75%; MS: 487.2 (M+1); HPLC (Conditions d, max plot): 98%, rt. 6.30 min.
$^1$H NMR (DMSO-d6) δ 10.86 (s, 1H), 9.28 (s, 1H), 7.72 (d, J=7.91 Hz, 1H), 7.68 (d, J=7.54 Hz, 1H), 7.51 (br t, 1H), 7.44-7.34 (m, 4H), 7.22-7.15 (m, 3H), 6.33 (d, J=7.53 Hz, 1H), 3.88-3.78 (m, 2H), 2.94-2.89 (m, 2H), 1.47 (s, 9H).

(2-{[2-(4-aminophenyl)ethyl]amino}pyrimidin-4yl) (1,3-benzothiazol-2-yl)acetonitrile (di TFA) (57)

Y=73%. (salt); MS: 387.2 (M+1); HPLC (Conditions c, max plot): 98.3%, rt. 3.02 min
$^1$H NMR (DMSO-d6) δ 7.93 (br d, 1H), 7.75-7.66 (m, 2H), 7.55 (br d, 1H), 7.43-7.36 (m, 3H), 7.26-7.17 (m, 3H), 6.40 (d, J=7.16 Hz, 1H), 4.9-4.2 (v br s, 1H), 3.94-3.82 (m, 2H), 2.99 (t, J=7.16 Hz, 2H).

1,3-benzothiazol-2-yl(2-{[2-(3,4-dimethoxyphenyl) ethyl]amino}pyrimidin-4-yl)acetonitrile (58)

Y=75%; MS: 432.0 (M+1); HPLC (Conditions c, max plot): 99%, rt. 4.26 min
$^1$H NMR (DMSO-d6) δ 7.85 (br t, 1H), 7.76-7.68 (m, 3H), 7.47-7.42 (m, 1H), 7.31-7.26 (m, 1H), 6.92-6.89 (m, 2H), 6.84-6.81 (m, 1H), 6.47 (d, J=6.78 Hz, 1H), 5.4-4.7 (very br s, 1H), 3.95-3.83 (m, 2H, 3.73 (s, 3H), 3.67 (s, 3H), 2.93 (t, J=7.16 Hz, 2H).

1,3-benzothiazol-2-yl(2-{[2-(3-methoxyphenyl) ethyl]amino}pyrimidin-4-yl)acetonitrile (59)

Y=76%; MS: 402.0 (M+1); HPLC (Conditions c, max plot): 99.9%, rt. 4.59 min
$^1$H NMR (DMSO-d6) δ 7.82 (br t, 1H), 7.75-7.69 (m, 2H), 7.62 (br d, 1H), 7.45-7.40 (m, 1H), 7.30-7.24 (m, 2H), 6.92-6.83 (m, 3H), 6.45 (d, J=7.16 Hz, 1H), 4.2-3.65 (m, 3H), 3.72 (s, 3H), 2.97 (t, J=7.16 Hz, 2H).

1,3-benzothiazol-2-yl(2-{[2-(2-fluorophenyl)ethyl] amino}pyrimidin-4-yl)acetonitrile (60)

Y=76%; MS: 390.2 (M+1); HPLC (Conditions c, max plot): 99.7%, rt. 4.41 min
$^1$H NMR (DMSO-d6) δ 7.88 (br t, 1H), 7.75-7.68 (m, 2H), 7.60 (br d, 1H), 7.45-7.40 (m, 2H), 7.33-7.16 (m, 4H), 6.44 (d, J=7.17 Hz, 1H), 4.20-3.60 (m, 3H), 3.04 (t, J=7.14 Hz, 2H).

1,3-benzothiazol-2-yl[2-({2-[3-(trifluoromethyl) phenyl]ethyl}amino)pyrimidin-4-yl]acetonitrile (61)

Y=84%; MS: 440.0 (M+1); HPLC (Conditions c, max plot): 99.3%, t 4.79 min
$^1$H NMR (DMSO-d6) δ 7.89 (br t, 1H), 7.75-7.54 (m, 7H), 7.46-7.41 (m, 1H), 7.29-7.24 (m, 1H), 6.45 (d, J=7.14 Hz, 1H), 4.45-3.70 (m, 3H), 3.11 (t, J=6.78 Hz 2H).

1,3-benzothiazol-2-yl{2-[(2-hydroxy-2-phenylethyl) amino]pyrimidin-4-yl}acetonitrile (TFA) (62)

Y=47% (salt); MS: 386.0 (M−1); HPLC (Conditions c, max plot): 99%, rt 3.87 min
$^1$H NMR (DMSO-d6) δ 7.83 (br t, 1H), 7.75-7.57 (m, 3H), 7.50-7.24 8 m, 9H), 6.42 (d, J=7.14 Hz, 1H), 4.90 (br t, 1H), 4.48-3.75 (m, 1H), 3.68-3.53 (m, 2H)

1,3-benzothiazol-2-yl{2-[(2-{[3-(trifluoromethyl) pyridin-2-yl]amino}ethyl)amino]pyrimidin-4-yl}acetonitrile (63)

Y=89%; MS: 456.2 (M+1); HPLC (Conditions c, max plot): 97.8%, rt 3.78 min
$^1$H NMR (DMSO-d6) δ 8.29-8.19 (m, 1H), 8.00 (br t, 1H), 7.87 (d, J=7.54 Hz, 1H), 7.77-7.72 (m, 3H), 7.48-7.43 (m, 1H), 7.32-7.27 (m, 1H), 6.70-6.58 (m, 2H), 6.78 Hz, 1H), 4.65-3.60 (m, 5H).

1,3-benzothiazol-2-yl(2-{[2-(3-chlorophenyl)ethyl] amino}pyrimidin-4yl)acetonitrile (TFA) (64)

Y=70% (salt); MS: 406.0 (M+1); HPLC (Conditions c, max plot): 99.7%, rt. 4.91 min
$^1$H NMR (DMSO-d6) δ 7.85-7.73 (m, 3H), 7.60 (br d, 1H), 7.41-7.24 (m, 7H), 6.44 (d, J=7.17 Hz, 1H), 3.98-3.50 (m, 3H), 3.04-2.99 (m, 2H).

1,3-benzothiazol-2-yl(2-{[2-(3,4-dichlorophenyl) ethyl]amino}pyrimidin-4-yl)acetonitrile (TFA) (65)

Y=56% (salt); MS: 440.0 (M+1); HPLC (Conditions c, max plot): 99.6%, rt. 5.15 min

1,3-benzothiazol-2-yl(2-{[2-(4-methoxyphenyl)ethyl]amino}pyrimidin-4-yl)acetonitrile (TFA) (66)

Y=69% (salt); MS: 402.0 (M+1); HPLC (Conditions c, max plot) 99.6%, rt. 4.33 min
¹H NMR (DMSO-d6) δ 7.75-7.69 (m, 3H), 7.61 (br d, 1H), 7.40-7.35 (m, 1H), 7.24-7.17 (m, 3H), 6.86 (d, J=8.28 Hz, 2H), 6.38 (d, J=7.16 Hz, 1H), 4.15-3.65 (m, 3H), 3.69 (s, 3H), 2.9-2.85 (m, 2H).

1,3-benzothiazol-2-yl(2-{[2-4-methylphenyl)ethyl]amino}pyrimidin-4-yl)acetonitrile (TFA) (67)

Y=72% (salt); MS: 386.0 (M+1); HPLC (Conditions c, max plot): 100% rt. 4.66 min
¹H NMR (DMSO-d6) δ 7.87 (br t, 1H), 7.76-7.67 (m, 3H), 7.47-7.42 (m, 1H), 7.32-7.27 (m, 1H), 7.23-7.14 (m, 4H), 6.47 (d, J=7.14 Hz, 1H), 4.20-3.55 (m, 3H), 2.98-2.93 (m, 2H), 2.30 (s, 3H).

1,3-benzothiazol-2-yl(2-{[2-(3-fluorophenyl)ethyl]amino}pyrimidin-4-yl)acetonitrile (TFA) (68)

Y=34% (salt); MS: 390.0 (M+1); HPLC (Conditions c, max plot): 98.4%, rt. 4.72 min
¹H NMR DMSO-d6) δ 7.90-7.67 (m, 3H), 7.57 (br d, 1H), 7.44-7.36 (m, 2H), 7.27-7.16 (m, 3H), 7.12-7.06 (m, 1H), 6.42 (d, J=7.14 Hz, 1H), 4.50-3.70 (m, 3H), 3.05-3.00 (m, 2H).

1,3-benzothiazol-2-yl(2-{[2-(4-phenoxyphenyl)ethyl]amino}pyrimidin-4-yl)acetonitrile (69)

Y=71%; MS: 464.2 (M+1); HPLC (Conditions c, max plot): 98%, rt. 5.34 min
¹H NMR (DMSO-d6) δ 7.80-7.68 (m, 3H), 7.60 (br d, 1H), 7.44-7.33 (m, 5H), 7.25-7.21 (m, 1H), 7.15-7.10 (m, 1H), 6.99-6.95 (m, 4H), 6.43 (d, J=6.78 Hz, 1H), 4.0-3.40 (m, 3H), 2.99 (t, J=6.78 Hz, 2H).

1,3-benzothiazol-2-yl(2-{[2-(2-phenoxyphenyl)ethyl]amino}pyrimidin-4-yl)acetonitrile (70)

Y=55%; MS: 464.2 (M+1); HPLC (Conditions c, max plot): 98%, rt. 5.29 min
¹H NMR (DMSO-d6) δ 7.88 (br t, 1H), 7.73 (d, J=7.92 Hz, 1H), 7.64 (br d, 1H), 7.58 (br d, 1H), 7.49-7.39 (m, 2H), 7.32-7.17 (m, 5H), 7.06-6.91 (m, 1H), 6.88-6.85 (m, 3H), 6.42 (d, J=6.78 Hz, 1H), 4.22-3.60 (m, 3H), 3.01 (t, J=6.78 Hz, 2H).

1,3-benzothiazol-2-yl(2-{[2-(4-bromophenyl)ethyl]amino}pyrimidin-4-yl)acetonitrile (71)

Y=96%; MS: 450.0 (M+1); HPLC (Conditions c, max plot): 99.6%, rt. 5.01 min
¹H NM (DMSO-d6) δ 7.81-7.68 (m, 3H), 7.60 (br d, 1H), 7.53 (d, J=8.28 Hz, 2H), 7.45-7.40 (m, 1H), 7.30-7.25 (m, 3H), 6.43 (d, J=7.16 Hz, 1H), 4.12-3.55 (m, 3H), 3.01-2.96 (m, 2H).

1,3-benzothiazol-2-yl(2-{[2-(4-fluorophenyl)ethyl]amino}pyrimidin-4-yl)acetonitrile (72)

Y=73%; MS: 389.8 (M+1); HPLC (Conditions c, max plot): 99.6%, rt. 4.72 min
¹H NMR (DMSO-d6) δ 7.75-7.70 (m, 3H), 7.59 (br d, 1H), 7.45-7.34 (m, 3H), 7.29-7.24 (m, 1H), 7.20-7.14 (m, 2H), 6.43 (d, J=7.17 Hz, 1H), 4.32-3.65 (m, 3H [2+1]), 2.99 (t, J=7.16 Hz, 2H).

1,3-benzothiazol-2-yl{2-[(2-[1,1'-biphenyl]-4-yl-ethyl)amino]pyrimidin-4-yl}acetonitrile (73)

Y=24%; MS: 448.2 (M+1); HPLC (Conditions c, max plot): 97.8%, it. 5.08 min
¹H (DMSO-d6) δ 8.00-7.63 (m, 7H), 7.49-7.33 (m, 6H), 726-7.21 (m, 1H), 6.44 (d, J=6.78 Hz, 1H), 4.15-3.40 (m, 3H[2+1]), 3.20-3.08 (m, 2H).

1,3-benzothiazol-2-yl{2-[(2-{4-[hydroxy(oxido)amino]phenyl}ethyl)amino]pyrimidin-4-yl}acetonitrile (74)

Y=33.8%; MS: 417.2 (M+1); HPLC (Conditions c, max plot): 98.7%, rt. 4.21 min
¹H NMR (DMSO-d6) δ 8.21 (d, J=8.66 Hz, 2H), 7.88 (br t, 1H), 7.75-7.68 (m, 2H), 7.61 (d, J=8.66 Hz, 2H), 7.54 (br d, 1H), 7.42-7.37 (m, 1H), 7.26-7.21 (m, 1H), 6.41 (d, J=7.17 Hz, 1H), 3.85-3.70 (m, 2H), 3.55-3.10 (m, 1H), 3.18-3.14 (m, 2H).

1,3-benzothiazol-2-yl(2-{[2-(1H-1,2,4-triazol-1-yl)ethyl]amino}pyrimidin-4-yl)acetonitrile (75)

Y=77.6%; MS: 361.2 (M−1); HPLC (Conditions c, max plot): 99.4%, rt. 2.79 min
¹H NMR (DMSO-d6) δ 8.59 (s, 1H), 8.09 (s, 1H), 7.93 (d, J=7.54 Hz, 1H), 7.75 (d, J=7.91 Hz, 1H), 7.67 (br d, 1H), 7.48-7.43 (m, 1H), 7.33-7.28 (m, 1H), 6.51 (d, J=7.16 Hz, 1H), 5.05-4.25 (m, 3H[2+1]), 4.10-3.98 (m, 2H).

1,3-benzothiazol-2-yl(2-{[3-1H-pyrazol-1-yl)propyl]amino}pyrimidin-4-yl)acetonitrile (76)

Y=70%; MS: 374.0 (M−1); HPLC (Conditions c, max plot): 94.8%, rt. 3.40 min
¹H NMR (DMSO-d6) δ 7.95 (d, J=7.91 Hz, 1H), 7.78-7.73 (m, 2H), 7.62 (br d, 1H), 7.46-7.43 (, 2H), 7.31-7.26 (m, 1H), 6.45 (d, J=7.17 Hz, 1H), 6.22 (s, 1H), 4.30-3.85 (m, 3H), 3.62-3.48 (m, 2H), 2.21-2.06 (m, 2H).

4-[2-({4-[1,3-benzothiazol-2-yl(cyano)methyl]pyrimidin-2-yl}amino)ethyl]benzene-sulfonamide (77)

Y=80%; MS: 449.0 (M−1); HPLC (Conditions c, max plot): 99%, rt. 3.28 min
¹H NMR (DMSO-d6) δ 11.20 (v br s, 1H, exchangeable), 7.81-7.65 (m, 5H), 7.57-7.50 (m, 3H), 7.44-7.22 (m, 4H), 6.43 (d, J=6.78 Hz, 1H), 4.10-3.80 (m, 2H), 3.20-3.00 (m, 2H).

{2-[(2-pyridin-3-ylethyl)amino]pyrimidin-4-yl}[5-(trifluoromethyl)-1,3-benzothiazol-2-yl]acetonitrile (di TFA) (78)

Y=30%; MS: 441.2 (M+1); HPLC (Conditions c, max plot): 96%, rt. 3.39 min

¹H NMR (DMSO-d6) δ 11.20 (v br s, 1H, exchangeable), 8.77 (d, J=1.88 Hz, 1H), 8.70-8.67 (m, 1H), 8.24 (d, J=7.91 Hz, 1H), 8.02-7.94 (m, 2H), 7.81-7.75 (m, 2H), 7.52-7.48 (m, 2H), 6.39 (d, J=7.14 Hz, 1H), 4.10-3.85 (m, 2H), 3.30-3.00 (m, 2H).

1,3-benzothiazol-2-yl{2-[(1H-tetraazol-5-ylmethyl)amino]pyrimidin-4-yl}acetonitrile (TFA) (79)

Y=31%; MS: 447.8 (M−1); HPLC (Conditions c, max plot): 99%, rt. 2.60 min.

¹H NMR (DMSO-d6) δ 8.40-8.29 (br d, 1H, exchangeable), 7.78-7.60 (m, 4H), 7.41-7.36 (m, 1H), 7.27-7.21 (m, 1H), 6.47 (d, J=6.78 Hz, 1H), 5.25-5.05 (m, 2H).

Example 3

Preparation of 1,3-benzothiazol-2yl[2-(benzyloxy)pyrimidin-4-yl]acetonitrile (80)

To a suspension of NaH (60% in oil, 0.056 g, 1.4 mmol) in dry DMA (1 ml) was added a solution of benzylalcohol (0.07 ml, 0.7 mmol) in dry DMA (1 ml) and the suspension was stirred 1 h at r.t. under inert atmosphere. A solution of 1 in DMA (1 ml) was added drop wise and the suspension was heated up to 100° C. under stirring and inert atmosphere ON. The reaction was cooled down and quenched by addition of water+NaCl saturated aqueous solution (up to 15 ml final volume). After 2 h at 4° C., the precipitate formed was filtered off and washed with water until neutral pH. The solid obtained was refluxed in acetonitrile, cooled down to r.t. then filtered off and washed with acetonitrile (3×). The residue was dried under vacuum at 40° C. ON, affording 0.082 g (33%) of the title compound as a yellow powder. mp 196-198° C., MS: 359.0 (M+1); HPLC (Conditions a, 262 nm): 99%, rt. 4.99 min.

¹HNMR (DMSO-d6) δ 12.74 (br s, 1H, exchangeable) 7.95 (d, J=7.53 Hz, 1H), 7.76-7.72 (m, 2H), 7.62-7.54 (m, 2H), 7.50-7.32 (m, 4H), 7.29-7.19 (m, 1H), 6.74-6.61 (br d, 1H), 5.68 (s, 2H)

Upon using the procedure described above in the example 4 and the appropriate starting material and reagents, the following additional benzothiazole derivatives of formula III could be obtained.

1,3-benzothiazol-2-yl{2-[(4-pyridin-3-ylbenzyl)oxy]pyrimidin-4-yl}acetonitrile (81)

Y=20%; MS: 436.0 (M+1); HPLC (Conditions c, max plot): 97%, rt. 3.43 min

¹H NMR (DMSO-d6) δ 9.05 (d, J=1.9 Hz, 1H), 8.71-8.68 (br d, 1H), 8.42-8.38 (m, 1H), 7.98-7.84 (m, 4H), 7.75-7.70 (m, 4H), 7.45-7.39 (m, 1H), 7.29-7.23 (m, 1H), 6.71 (br d, 1H), 5.77 (s, 2H), 5.15-3.50 (m, 1H).

1,3-benzothiazol-2-yl[2-(pyridin-4-ylmethoxy)pyrimidin-4-yl]acetonitrile (TFA) (82)

Y=20%; MS: 360.2 (M+1); HPLC (Conditions c, max plot): 97.9%, rt. 2.91 min

¹H NMR (DMSO-d6) δ 8.77 (dd, J=6.41 Hz, 1.51 Hz, 2H), 8.01 (br d, 1H), 7.94 (d, J=7.91 Hz, 1H), 7.86 (d, J=6.41 Hz, 2H), 7.70 (d, J=7.91 Hz, 1H), 7.46-7.40 (m, 1H), 7.30-7.25 (m, 1H), 6.79 (br d, 1H, 5.85 (s, 2H), 5.15-3.80 (m, 1H).

1,3-benzothiazol-2-yl[2-(pyridin-2-ylmethoxy)pyrimidin-4-yl]acetonitrile (TFA) (83)

Y=42% (salt); MS: 360.0 (M+1); HPLC (Conditions c, 254 nm): 96%, rt. 3.30 min

¹H NMR DMSO-d6) δ 8.66 (d, J=4.9 Hz, 1H), 7.97-7.88 (m, 3H), 7.74-7.64 (m, 2H), 7.46-7.39 (m, 2H), 7.28-7.23 (m, 1H), 6.74 (d, J=6.03 Hz, 1H), 5.76 (s, 2H).

1,3-benzothiazol-2-yl[2-(3-pyridin-2-ylpropoxy)pyrimidin-4yl]acetonitrile (TFA) (84)

Y=33% (salt); MS: 386.0 (M−1); HPLC (Conditions c, max plot) 88%, rt. 2.93 min

¹H NMR (DMSO-d6) δ 8.98 (d, J=5.27 Hz, 1H), 8.20-8.15 (m, 1H), 7.91 (d, J=7.54 Hz, 1H), 7.76-7.74 (m, 3H), 7.62-7.58 (m, 1H), 7.45-7.38 (m, 1H), 7.30-7.25 (m, 1H), 6.66 (d, J=6.41 Hz, 1H), 4.69 (t, J=6.03 Hz, 2H), 3.12 (t, J=7.54 Hz, 2H), 2.35-2.27 (m, 2H).

1,3-benzothiazol-2-yl {2-[(4-methoxybenzyl)oxy]pyrimidin-4-yl}acetonitrile (85)

Y=61%; MS: 387.0 (M−1); HPLC (Conditions d, max plot): 98%, rt. 5.74 min

¹H NMR (DMSO-d6) δ 12.69 (br s, 1H, exchangeable), 7.92 (d, J=7.54 Hz, 1H), 7.77-7.70 (m, 2H, 7.50 (d, J=8.66 Hz, 2H), 7.41-7.55 (m, 1H), 7.24-7.18 (m, 1H), 6.98 (d, J=8.67 Hz, 2H), 6.63 (d, J=6.4 Hz, 1H, 5.60 (s, 2H), 3.76 (s, 3H).

1,3-benzothiazol-2-yl[2-(pyridin-3-ylmethoxy)pyrimidin-4-yl]acetonitrile (TFA) (86)

Y=65% (salt); MS: 357.8 (M−1); HPLC (Conditions c, max plot): 99%, rt. 2.86 min

¹H NMR (DMSO-d6) δ 8.91 (d, J=1.51 Hz, 1H), 8.71-8.68 (m, 1H), 8.23 (d, J=7.91 Hz, 1H), 7.95-7.93 (m, 2H), 7.74-7.65 (m, 2H), 7.45-7.40 (m, 1H), 7.29-7.24 (m, 1H), 6.75 (d, J=6.39 Hz, 1H), 5.76 (s, 3H), 5.9-5.0 (very br s, 1H).

1,3-benzothiazol-2-yl{2-[2-(4-methoxyphenyl)ethoxy]pyrimidin-4-yl}acetonitrile (87)

Y=27%; MS: 400.8 (M−1); HPLC (Conditions d, max plot): 95%, rt. 5.79 min

¹H NMR (DMSO-d6) δ 12.65 (br s, 1H, exchangeable), 7.82-7.70 (m, 3H), 7.42-7.36 (m, 1H), 7.30-7.20 (m, 3H), 6.90 (d, J=8.28 Hz, 2H), 6.60 (d, J=6.4 Hz, 1H), 4.85-4.80 (m, 2H), 3.73 (s, 3H), 3.12-3.07 (m, 2H).

1,3-benzothiazol-2-yl[2-([1,1'-biphenyl]-3-ylmethoxy)pyrimidin-4-yl]acetonitrile (88)

Y=40%; MS: 433.0 (M−1); HPLC (Conditions c, max plot): 98%, rt. 7.12 min

¹H NMR (DMSO-d6) δ 12.74 (br s, 1H), 7.95-7.92 (m, 2H), 7.75-7.67 (m, 4H), 7.56-7.37 (m, 6H), 7.26-7.21 (m, 1H), 6.67 (br d, 1H), 5.77 (s, 2H).

1,3-benzothiazol-2-yl{2[(3,4,5-trimethoxybenzyl)oxy]pyrimidin-4-yl}acetonitrile (89) 11998

Y=18%; MS: 447.0 (M−1); HPLC (Conditions c, max plot): 92%, rt. 5.24 min

¹H NMR (DMSO-d6) δ 12.71 (br s, 1H), 7.95 (d, J=8.18 Hz, 1H), 7.90-7.72 (m, 2H), 7.43-7.37 (m, 1H), 7.27-7.21 (m, 1H), 6.94 (s, 2H), 6.67 (br d, 1H), 5.59 (s, 2H), 3.77 (s, 6H), 3.65 (s, 3H).

1,3-benzothiazol-2-yl{2-[(3,4dichlorobenzyl)oxy]pyrimidin-4-yl}acetonitrile (90)

Y=5%; MS: 424.8 (M−1); HPLC (Conditions c, max plot): 98%, rt. 6.79 min
¹H NMR (DMSO-d6) δ 7.82-7.72 (m, 3H), 7.64 (d, J=7.91 Hz, 1H), 7.50-7.46 (m, 2H), 7.24-7.21 (m, 1H), ), 7.01-6.96 (m, 1H), 6.53-6.50 (br d, 1H), 5.51 (s, 2H).

1,3-benzothiazol-2-yl[2-({3-[(dimethylamino)methyl]benzyl}oxy)pyrimidin-4-yl]acetonitrile (TFA) (91)

Y=28%; MS: 416.2 (M+1); HPLC (Conditions c, max plot): 98%, rt. 2.96 min
¹H NMR (DMSO-d6) δ 9.79 (br s, 1H, exchangeable), 7.93-7.90 (m, 2H), 7.74-7.39 (m, 7H), 7.29-7.23 (m, 1H), 6.73 (d, J=6.11 Hz, 1H), 5.71 (s, 2H), 4.30 (s, 2H), 2.72 (s, 6H)

1,3-benzothiazol-2-yl{2-[(1-oxidopyridin-3-yl)methoxy]pyrimidin-4-yl}acetonitrile (92) 12149

Y=16%; MS: 3.74.0 (M−1); HPLC (Conditions c, max plot): 90%, rt. 2.78 min
¹H NMR (DMSO-d6) δ 9.95 (br s, 1H, exchangeable), 7.94-7.64 (m, 6H), 7.56-7.53 (m, 2H), 7.45-7.39 (m, 1H), 7.29-7.23 (m, 1H), 6.72 (br d, 1H), 5.73 (s, 2H), 4.35 (s, 2H), 4.05-3.00 (m, 8H)

1,3-benzothiazol-2-yl(2-{[4-(morpholin-4-ylmethyl)benzyl]oxy}pyrimidin-4-yl)acetonitrile (TFA) (93)

Y=20%; MS: 458.2 (M+1); HPLC (Conditions c, max plot): 99%, rt. 2.80 min
¹H NMR (DMSO-d6) δ 8.47 (s, 1H), 8.22 (d, J=6.03 Hz, 1H), 7.98-7.94 (m, 2H), 7.31 (d, J=8.28 Hz, 1H), 7.62-7.33 (m, 3H), 7.30-7.26 (m, 1H), 6.82-6.68 (br d, 1H), 5.64 (s, 2H).

1,3-benzothiazol-2-yl{2-[(4-pyridin-2-ylbenzyl)oxy]pyrimidin-4-yl}acetonitrile (TFA) (94)

Y=34%; MS: 435.0 (M+1); HPLC (Conditions c, max plot): 99%, rt. 3.22 min
¹H NMR (DMSO-d6) δ 8.80 (d, J=4.14 Hz, 1H), 8.24-7.79 (m, 10H), 7.55-7.49 (m, 2H), 7.39-7.33 (m, 1H), 6.82 (br d, 1H), 5.89 (s, 2H).

1,3-benzothiazol-2-yl(2-{[(piperdin-1-ylmethyl)benzyl]oxy}pyrimidin-4-yl)acetonitrile (TFA) (95)

Y=15%; MS: 456.2 (M+1); HPLC (Conditions c, max plot): 97%, rt. 3.00 min
¹H NMR (DMSO-d6) δ 9.27 (br s, 1H, exchangeable), 7.93-7.39 (m, 10H), 7.28-7.22 (m, 1H), 6.72 (br d, 1H), 5.73 (s, 2H), 4.28 (d, J=4.9 Hz, 1H), 3.80-3.20 (m, 2H), 2.90-2.78 (m, 2H), 1.79-1.27 (m, 6H).

Example 4

Preparation of 1,3-benzothiazol-2-yl[2-(4-methoxyphenoxy)pyrimidin-4-yl]acetonitrile (96)

To a solution of 1 (0.300 g, 1.05 mmol) in DMSO (7 ml) were added 4-methoxyphenol (0.261 g, 2.1 mmol) and cesium carbonate (1.7 g, 5.25 mmol) and the suspension was shaken at 100° C. for 8 days. After cooling to r.t., the suspension was poured onto ice/water and the product was extracted with AcOEt. The organic phases were washed with water then brine, dried over MgSO4 and concentrated to dryness. The residue was triturated in hot EtOH then filtered off and dried under vacuum at 50° C. overnight, affording 202 mg (51%) of the title compound.

MS: 375.0 (M+1); HPLC (Conditions c, max plot): 99%/o, rt. 5.21 min
¹H NMR (DMSO-d6) δ 8.16 (br d, 1H), 7.60 (d, J=8.29 Hz, 1H), 7.45-7.37 (m, 2H), 7.28-7.23 (m, 3H), 7.11-7.08 (m, 2H), 6.83 (br d, 1H), 3.86 (s, 3H).

Upon using the procedure described above in the example 4 and the appropriate starting material and reagents, the following additional benzothiazole derivatives of formula III could be obtained.

1,3-benzothiazol-2-yl[2-(4-butoxyphenoxy)pyrimidin-4-yl]acetonitrile (97)

Y=42%; MS: 415.0 (M−1); HPLC (Conditions c, max plot): 90%, rt. 6.16 min
¹H NMR (DMSO-d6) δ 12.97 (br s, 1H, exchangeable), 8.20-8.05 (br d, 1H), 7.60-7.56 (br d, 1H), 7.44-7.34 (m, 2H), 7.22-7.16 (m, 3H), 7.10-7.05 (m, 2H), 6.79 (d, J=5.65 Hz, 1H), 4.03 (m, 2H), 1.75 (m, 2H), 1.50 (m, 2H), 0.97 (m, 3H).

{2-[4-(4-acetylpiperazin-1-yl)phenoxy]pyrimidin-4-yl}(1,3-benzothiazol-2-yl)acetonitrile (98)

Y=8.5%; MS: 469.2 (M−1); HPLC (Conditions c, max plot): 94.8%, rt. 4.10 min
¹H NMR (DMSO-d6) δ 8.18-8.10 (m, 1H), 7.60-7.52 (m, 2H), 7.41-7.36 (m, 1H), 7.28-7.10 (m, 5H), 6.83 (br d, 1H), 3.23-3.17 (m, 4H), 2.07 (s, 3H).

[2-(4-methoxyphenoxy)pyrimidin-4-yl][5-(trifluoromethyl)-1,3-benzothiazol-2-yl]acetonitrile (99)

Y=33%; MS: 443.2 (M+1); HPLC (Conditions c, max plot): 99%, rt. 6.09 min
¹H NMR (DMSO-d6) δ 8.04-7.89 (m, 2H), 7.61-7.53 (m, 2H), 7.32 (d, J=9.05 Hz, 2H), 7.12 (d, J=9.05 Hz, 2H), 6.83 (d, J=6.40 Hz, 1H), 3.87 (s, 3H).

Example 5

1,3-benzothiazol-2-yl(pyrimidin-4-yl)acetonitrile (100)

To a solution of 1 (0.1 g, 0.35 mmol) in acetic acid was added sodium acetate (29 mg, 0.35 mmol) and palladium on charcoal (20 mg). The suspension was heated up to 70° C. under hydrogen at 3.5 bar for 3 h. After cooling to rt., the suspension was filtered through celite and the acetic acid evaporated. The bright yellow powder was taken up in ethyl acetate and aqueous sodium hydroxide 10%. After 3 extractions the organic phases were thoroughly washed with brine then dried over MgSO4 and concentrated to dryness. After purification by preparative HPLC and drying under vacuum at 50° C., 12 mg (13%) of the title compound were obtained as a yellow powder.

MS: 253.2 (M+1); HPLC (Conditions c, max plot): 98%, rt. 3.35 min

¹H NMR (DMSO-d6) δ 8.61 (s, 1H), 8.00-7.73 (m, 3H), 7.44-7.39 (in 1H), 7.29-7.23 (m, 1H), 6.90 (br d, 1H), 3.87 (s, 3H).

Example 6

N-[2-({4-[1,3-benzothiazol-2-yl(cyano)methyl]pyrimidin-2-yl}amino)ethyl]-4-chlorobenzamide (TFA salt) (101)

To a solution of 46 (0.1 g, 0.32 mmol) in DCM/DMF 3/1 (4 ml) was added p-chloro benzoylchloride (0.056 g, 0.32 mmol) and triethylamine (0.09 ml, 0.64 mmol) and the solution was shaken overnight at r.t then at 40° C. for 3 h. After cooling down to r.t, the precipitate formed was filtered off then washed with DCM then water. After recrystallization in acetonitrile, 98 mg (68%) of the title compound (base) was obtained as a yellow powder.

The product was taken up in a mixture of DCM/TFA. The yellow fluffy solid formed by addition of ether was filtered off, washed with ether (3×) then dried under vacuum at 40° C., affording 105 mg of the title compound as a yellow powder:

MS: 449.2 (M+1); HPLC (Conditions c, max plot): 95%, rt. 3.99 mm

¹H NMR (DMSO-d6) δ 8.80-8.75 (m, 1H), 7.96-7.41 (m, 9H), 7.31-7.25 (m, 1H), 6.47 (d, J=6.78,1H), 4.50-3.30 (m, 5H).

Example 7

Preparation of 1,3-benzothiazol-2-yl(2-methoxy-4-pyrimidinyl)-acetonitrile (102)

To a suspension of 1 (0.1 g, 0.35 mmol) in dry MeOH (3 ml) was added MeONa (0.08 g, 1.4 mmol) and Et₃N (0.05 ml, 0.35 mmol) and the suspension was warmed up to 60° C. for 6 days. The solid present was filtered off and the filtrate concentrated to near dryness. The solid residue obtained was washed with water until neutral pH, then dried under vacuum at 40° C. to afford 44 mg (45%) of the title compound as a yellow powder.: mp 234. ° C. dec., MS: 283 (M+1); HPLC (Conditions a, 262 nm) 97%, rt. 3.40 min;

¹HNMR (DMSO-d6) δ 7.79 (d, J=4.52 Hz, 1H), 7.78 (d, J=7.91 Hz, 1H), 7.55 (d, J=7.91 Hz, 1H), 7.29-7.23 (m, 1H), 7.07-7.02 (m, 1H), 6.53 (br d, 1H), 4.02 (s, 3H)

Example 8

Preparation of a Pharmaceutical Formulation

The following formulation examples illustrate representative pharmaceutical compositions according to the present invention being not restricted thereto.

Formulation 1—Tablets

A benzazole compound of formula I is admixed as a dry powder with a dry gelatin binder in an approximate 1:2 weight ration. A minor amount of magnesium stearate is added as a lubricant. The mixture is formed into 240-270 mg tablets (80-90 mg of active benzazole compound per tablet) in a tablet press.

Formulation 2—Capsules

A benzazole compound of formula I is admixed as a dry powder with a starch diluent in an approximate 1:1 weight ratio. The mixture is filled into 250 mg capsules (125 mg of active benzazole compound per capsule).

Formulation 3—Liquid

A benzazole compound of formula I (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A benzazole compound of formula I is admixed as a dry powder with a dry gelatin binder in an approximate 1:2 weight ratio. A minor amount of magnesium stearate is added as a lubricant. The mixture is formed into 450-900 mg tablets (150-300 mg of active benzazole compound) in a tablet press.

Formulation 5—Injection

A benzazole compound of formula I is dissolved in a buffered sterile saline injectable aqueous medium to a concentration of approximately 5 mg/ml.

Example 9

Biological Assays

Those of skill in the art can readily identify a variety of assays that can be used to assess the activity of benzazole compounds of the invention. The below specified assays are cited as examples to assess the suitability of the benzazole compounds of the invention for the modulation of JNK and thus to modulate apoptosis.

JNK2 and 3 enzyme assay: JNK3 and/or JNK2 assays are performed in 96 well MTT plates, by incubation of 0.5 µg of recombinant, pre-activated GST-JNK3 or GST-JNK2 with 1 µg of recombinant, biotinylated GST-c-Jun and 2 µM ³³γ-ATP (2 nCi/µl), in the presence or absence of one or more benzazole inhibitors and in a reaction volume of 50 µl containing 50 mM Tris-HCl, pH 8.0; 10 mM MgCl₂; 1 mM Dithiothreitol, and 100 µM Na₃VO₄. The incubation is performed for 120 min. at R.T and stopped upon addition of 200 µl of a solution containing 250 µg of Streptavidine-coated SPA beads (Amersham, Inc.)*, 5 mM EDTA, 0.1% Triton X-100 and 50 µM ATP, in phosphate saline buffer. After incu-bation for 60 minutes at RT, beads are sedimented by centrifugation at 1500 ×g for 5 minutes, resuspended in 200 µl of PBS containing 5 mM EDTA, 0.1% Triton X-100 and 50 µM ATP and the radioactivity measured in a scintillation β counter, following sedimentation of the beads as described above. By substituting GST-c Jun for biotinylated GST-₁ATF² or myelin basic protein, this assay can be used to measure inhibition of preactivated p38 and ERK MAP Kinases, respectively.

Representative values for some exemplary compounds are given in the table shown below:

| Compound No | JNK3 IC$_{50}$ (nM) | JNK2 IC$_{50}$ (nM) | p38 IC$_{50}$ (nM) | ERK2 IC$_{50}$ (nM) |
|---|---|---|---|---|
| 1 | 290 | 500 | >30000 | >30000 |
| 4 | 350 | 970 | >30000 | >30000 |
| 10 | 70 | 210 | >30000 | >30000 |
| 15 | 950 | 2300 | >30000 | >30000 |
| 23 | 510 | 1800 | >30000 | >30000 |
| 80 | 60 | 250 | >30000 | >30000 |
| 96 | 30 | 300 | >30000 | >30000 |
| 102 | 105 | 450 | >30000 | >30000 |

The values indicated in respect of JNK2 and 3, p38 and ERK2 refer to the $IC_{50}$ (nM), i.e. the amount necessary to achieve 50% inhibition of the target (e.g. JNK2 or 3). The compound no. denotes a test compound as set out with its number in the above examples. From the above table it could be derived that the test compounds do have a significant effect both on JNK2 and more notably on JNK 3, but virtually no effect onto p38 and ERK2, thus delivering a quite selective inhibitory effect.

The tested compounds according to formula I display an inhibition ($IC_{50}$) with regard to JNK3 of less than 10 μM, more preferred less than 0.1 μM.

In the following, the in vitro and in vivo assays are set out to which the compounds according the present invention may be subjected to confirm their JNK inhibitory and thus apoptosis regulating (i.e. inhibitory) activity.

A. Sympathetic Neuron Culture and Survival Assay (in vitro)

Sympathetic neurons from superior cervical ganglia (SCG) of new-born rats (p4) are dissociated in dispase, plated at a density of $10^4$ cells/cm$^2$ in 48 well MTT plates coated with rat tail collagen, and cultured in Leibowitz medium containing 5% rat serum, 0.75 μg/mL NGF 7S (Boehringer Mannheim Corp., Indianapolis, Ind.) and arabinosine $10^5$M. Cell death is induced at day 4 after plating by exposing the culture to medium containing 10 μg/m. of anti NGF antibody (Boehringer Mannheim Corp., Indianapolis, Ind.) and no NGF or arabinosine, in the presence or absence of benzazole inhibitors. 24 hours after cell death induction, determination of cell viability is performed by incubation of the culture for 1 hour, at 37° C. in 0.5 mg/mL of 3-(4,5-dimethylthiazol-2-yl)2,5 diphenyl tetrazolium bromide (MTT). After incubation in MTT cells are resuspended in DMSO, transferred to a 96 MTT plate and cell viability is evaluated by measuring optical density at 590 nm. This assay demonstrates that compounds of Formula I (e.g. compounds (1), (25), (90)) rescue neurons from cell death (neuronal survival rate of up to 80%)

B. Il-2 Release Assay (in vitro)

Jurkat cells, a human T cell leukemia cell line (American Type Culture Collection #TIB 152) were cultured in RPMI 1640 medium (Gibco, BRL) supplemented with 10% of heat-activated FCS, Glutamine and Penstrep. The cell suspension in the medium is diluted to give $2.10^6$ cells/mL. The cells were plated ($2.10^5$ cells/well) on a 96-well plate containing different concentration of test compound (final concentration of compounds, 10, 3, 1, 0.3, 0.1 μM). This mixture is incubated 30 minutes at 37° C. in a humidified $CO_2$ atmosphere. Cells were then treated with 10 μl PMA+Ionomycine (0.1 μM and 1 μM final concentration) in all wells except negative control. In wells without compounds, 10 μl of RPMI 2% DMSO (=0.1% final) is added. Cells are incubated 24 hours at 37° C. and then the supernatant harvested (freeze at −20° C. if not used the same day) prior to performing IL-2 ELISA test on the supernatant.

B1. IL-2 ELISA Assay (in vitro)

IL-2 release into the medium by PMA+Iono-stimulated Jurkat cells, in presence or absence of test compounds is assayed by ELISA. Following the procedure described below:

Solutions:
Wash buffer: PBS-Tween 0.05%
Diluent: PBS-Tween 0.05%
Substrate solution: Citric acid 0.1M/$Na_2HPO_4$ 0.1M
Stop solution: $H_2SO_4$ 20%
Matched Antibody Pairs/Standard:
From R&D Systems B2. Monoclonal Anti-Human IL-2 Antibody (MAB602) (Capture)
Biotinylated anti-human IL-2 antibody (BAF202) (detection)
Recombinant human IL-2 (202-IL-010) (standard)
Plate Preparation
Transfer 100 μl capture antibody diluted in PBS at 5 μg/mL into a 96 well ELISA plate and incubate overnight at room temperature.
Aspirate each well and wash 3 times with Wash buffer. After the last wash, damp the plate.
1. Saturate with 200 μl PBS-10% FCS. Incubate 1 hour at room temperature.
2. Repeat the wash step 2.
Assay Procedure
1. Add 100 μl of sample or standard (2000, 1000, 500, 250, 125, 62.5, 31.25 pg/mL) and incubate 2 hours at room temperature.
2. Wash 3 times.
3. Add 100 μl of biotinylated anti-human IL-2 at 12.5 ng/mW. Incubate 2 hours at room temperature.
4. Wash 3 times.
5. Add 100 μl streptavidin-HRP (Zymed #43-4323) at 1:10,000. Incubate 30 minutes at room temperature.
6. Wash 3 times
7. Add 100 μl substrate solution (citric acid/$Na_2HPO_4$ (1:1)+$H_2O_2$ 1:2000+OPD). Incubate 20-30 minutes at room temperature.
8. Add 50 μl of stop solution to each well.
9. Determine optical density using a microtiter plate reader set to 450 nm with correction at 570 nm.

Following to this assay the compounds of formula I (e.g. compounds (1), (10), (83)) decrease the production of IL-2 of more than 30% at 3 μM. Thus, a reduction of the level of inflammatory cytokines is obtained by using compounds of formula I.

C. C-Jun Reporter Assay (in vitro)

Cell Culture

Hlr c-Jun HeLa cells are cultured in DMEM High Glc supplemented with 10% FCS (Sigma), 2 mM Glutamine (Gibco), P/S, Hygromycin b 100 μg/mL and G418 250 μg/mL Cell Culture Preparation Cell Banks The cells are stored frozen in cryotubes under liquid nitrogen, as 1.8 mL volumes of cell suspension in culture medium containing 10% dimethyl sulfoxide.

Cells are kept in culture for no more than 20 passages.

Cell Culture Thawing

When necessary, frozen vials of cells are thawed rapidly at 37° C. in a water bath by gently swirling up to semi-complete thawing. Then the cell suspension are added to 10 mL of culture medium. The cell suspension is then centrifuged for 5 minutes at 1200 rpm, the supernatant is removed and the cell pellet reconstituted in the medium and add to a 175 cm$^2$ flask containing 25 mL medium. The flasks are incubated at 37° C. in an atmosphere of 5% $CO_2$.

Cell Passage

The cells are serially subcultured (passaged) when 80% confluent monolayers have been obtained. The medium of each flask is removed and the monolayer is washed with 10-15 mL of phosphate buffer solution (PBS). Trypsin-EDTA solution is added to the cell mono-layer, incubated at 37° C. and tapped gently at intervals to dislodge the cells.

Complete detachment and disaggregation of the cell monolayer is confirmed by microscopy examination. The cells are then resuspended in 10 mL of complete medium and centrifuged for 5 minutes at 1200 rpm. The supernatant are discarded, the cells are resuspended in culture medium and diluted 1/5 in 175 cm² flasks.

Day 0 Morning

Prepare Cells for Transfections

The cells from flasks of near-confluent cultures are detached and disaggregated by treat-ment with trypsin as described above. The cells are resuspended in culture medium and counted. The cell suspension are diluted with medium to give about $3.5 \times 10^6$ cells/mL and 1 mL of cell suspension are put onto 2 10 cm culture dishes containing 9 mL of culture medium. The plates are incubated at 37° C. in a humidified atmosphere of 5% $CO_2$ in air.

Day 0 Evening

Transfections

| | |
|---|---|
| Control | 0.2 µg pTK Renilla, 5.8 µg pBluescript KS, 500 µl OPTIMEM (GIBCO), 18 µl Fugene 6 |
| Induced | 0.1 µg pMEKK1, 0.2 µg pTK Renilla, 5.7 µg pBluescript KS, 500 µl OPTIMEM (GIBCO), 18 µl Fugene 6 30' RT |

The transfection mixture is added to the plated cells. The plates are incubated over night at 37° C. in a humidified atmosphere of 5% $CO_2$ in air Day 1

A 96 wells plate containing 100 µl of culture medium per well is prepared Negative control (vehicle): 2 µl of DMSO is added to the 100 µl(in triplicate). Compound: 2 µl of Hit compound stock dilution are added to the 100 µl(in triplicate). The transfected cells are trypsinised and re-suspend in 12 mL of culture medium 100 µl of the dilution are added to each of the 96 wells plate. The plate is incubated over night at 37° C. in a humidified atmosphere of 5% $CO_2$ in air Hit Compound Dilutions Hit compound stock concentrations are the following: 3, 1 and 0.1 nM in 100% DMSO.

Day 2

Test Procedure

Dual-Luciferase™ Reporter Assay System (Promega)

The medium is removed from the plate and the cells washed two times with 100 µl PBS Completely remove the rinse solution before applying PLB reagent. Dispense into each culture well 5 µl of 1× PLB. Place the culture plates on a rocking platform or orbital shaker with gentle rocking/shaking to ensure complete and even coverage of the cell monolayer with 1× PLB. Rock the culture plates at room temperature for 15 minutes. Transfer 20 µl of the lysate into a white opaque 96 wells plate. Read in a luminometer.

Inject 50 µl of Luciferase Assay Reagent II wait 5", read 10"

Inject 50 µl of Stop & Glo® Reagent wait 5", read 10"

Check RLU Luciferase/RLU Renilla*1000

This assay shows that test compounds of Formula I (e.g. compounds (33), (93), (95)) inhibit more than 50% of the activity of JNK at 10 µM. Thus, the assay demonstrates the suitability of the compounds according to formula I to down-regulate apoptosis.

D. LPS Induced Endotoxin Shock in Mice (in vivo)

The ability of the JNK inhibitors described in formula I to significantly reduce the level of inflammatory cytokines induced by LPS challenge may be assessed using the following protocol:

LPS (S. abortus-Galanos Lab.-) was injected (200 µg/kg, i.v.) to Male C57BL/6 to induce endotoxin shock and compounds (0.1, 1, 10, 30 mg/kg) or NaCl (200 uM) were injected intravenously (10 mL/kg) 15 min before the LPS challenge. Heparinized blood was obtained from the orbital sinus at different time points after the LPS challenge, and the blood was centrifuged at 9,000 rpm for 10 min at 4° C. to collect supernatant for the measurement of cytokines production by mouse ELISA kit such as IFNγ (Duoset R&D Ref. DY485).

E. Global Ischemia in Gerbils (in vivo)

The ability of the JNK inhibitors described in formula I to protect cell death during a stroke event may be assessed using the following protocol:

1—Method

Surgery

Anesthesia: halothane or isoflurane (0.5-4%).

Sheaving of the gorge and incision of the skin.

The common carotid arteries (left and right) are freed from tissue.

Occlusion of the arteries using Bulldog microclamps during 5 min.

Disinfection of the surgery plan (Betadine®) and suture of the skin (Autoclip® or Michel's hooks).

Stabulation of the animals under heating lamp until awake.

Stabulation of the animals in the animalry in individual cages.

Sacrifice of the Animals 7 days after ischemia (Decapitation or overdose of pentobarbital).

Sampling of the brain.

Histological Parameters

Freezing of the brain in isopentane (−20° C.)

Slicing of the hippocampus using a cryo-microtome (20 µm).

Staining with cresyl violet and/or TUNEL method

Evaluation of the lesions (in CA1/CA2 subfields of the hippocampus)

Gerhard & Boast score modified or

Cell counting in the CA1/CA2

Biochemical Parameters

Microdissection of the cerebral structures

Parameters determined: DNA fragmentation, lactate, calcium penetration.

Analytical methods: ELISA, colorimetry, enzymology, radiometry.

2—Treatment

Administration of the test article or the vehicle: 15 min after reperfusion (5-10 min after the recovery of the anesthesia).

Standard Protocol 50 animals: 5 groups of 10 (group A: control groups B-D: test article at 3 doses and group E: reference compound ketamine 3×120 mg/kg, ip or Orotic acid 3×300 mg/kg, ip).

The invention claimed is:

1. A benzothiazole compound according to formula I

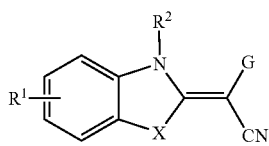

as well as its tautomers, its geometrical isomers, its optically active forms as enantiomers, diastereomers and its racemate forms, as well as pharmaceutically acceptable salts thereof, wherein:

G is an unsubstituted or substituted pyrimidinyl group;
$R^1$ is selected from the group consisting of hydrogen, $C_1$-$C_6$-alkyl, optionally substituted by halogen;
$R^2$ is hydrogen;
with the proviso that if $R^1$ is H, G may be neither of the following pyrimidines:

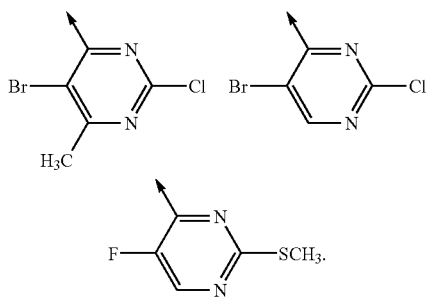

2. A benzothiazole compound according to claim 1 of formula I, as well as their tautomers according to formula II below,

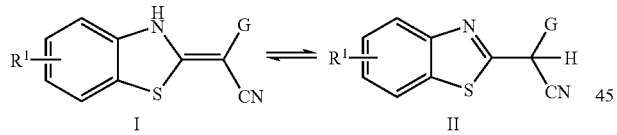

their geometrical isomers, their optically active forms as enantiomers, diastereomers and their racemate forms, as well as pharmaceutically acceptable salts thereof.

3. A benzothiazole compound according to claim 1, wherein:

G is a pyrimidinyl group

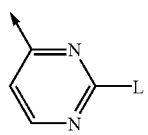

L is selected from the group consisting of hydrogen, unsubstituted or substituted $C_1$-$C_6$ alkyl, unsubstituted or substituted $C_1$-$C_6$ alkoxy, unsubstituted or substituted $C_1$-$C_6$ thioalkoxy, unsubstituted or substituted $C_2$-$C_6$ alkenyl, unsubstituted or substituted $C_2$-$C_6$ alkynyl, primary, secondary or tertiary amino groups, aminoacyl, aminocarbonyl, amino-($C_1$-$C_{10}$)alkyl, amino-unsubstituted or substituted ($C_1$-$C_{10}$)-alkyl-aryl, amino-unsubstituted or substituted ($C_1$-$C_{10}$)alkyl-heteroaryl, unsubstituted or substituted $C_1$-$C_6$ alkoxycarbonyl, carboxyl, cyano, halogen, hydroxy, nitro, sulfoxy, sulfonyl, unsubstituted or substituted aryl, unsubstituted or substituted heteroaryl, unsubstituted or substituted 3-8 membered cycloalkyl, optionally containing at least one heteroatom selected from N, O, S, and unsubstituted or substituted hydrazido groups, wherein the term "substituted" means that said groups can be substituted with from 1 to 5 substituents selected from the group consisting of $C_1$-$C_6$-alkyl, $C_1$-$C_6$-alkyl aryl, $C_1$-$C_6$-alkyl heteroaryl, $C_2$-$C_6$-alkenyl, $C_2$-$C_6$-alkynyl, primary, secondary or tertiary amino groups or quarternary ammonium moieties, acyl, acyloxy, acylamino, aminocarbonyl, alkoxycarbonyl, aryl, heteroaryl, carboxyl, cyano, halogen, hydroxyl, mercapto, nitro, sulfoxy, sulfonyl, alkoxy, thioalkoxy, and trihalomethyl; and said substitution may optionally include situations where neighboring substituents have undergone ring closure wherein said substituents form lactams, lactones, cyclic anhydrides, acetals, thioacetals, or aminals formed by ring closure.

4. A benzothiazole compound according to claim 3, wherein L is a group —N($R^a$, $R^b$) or —O$R^a$, with $R^a$ and $R^b$ being each independently selected from the group consisting of H, unsubstituted or substituted ($C_1$-$C_{10}$)-alkyl, unsubstituted or substituted $C_1$-$C_6$ alkyl-aryl, unsubstituted or substituted $C_1$-$C_6$-alkyl-heteroaryl, unsubstituted or substituted aryl, heteroaryl and unsubstituted or substituted 4-8 membered saturated or unsaturated cycloalkyl.

5. A benzothiazole compound according to claim 4 wherein L is selected from

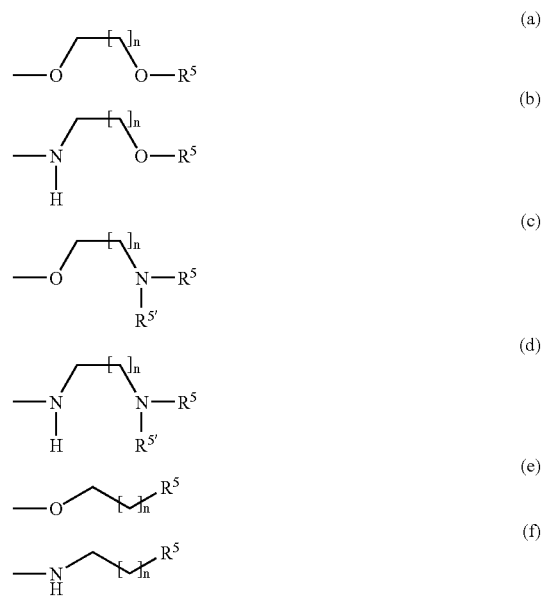

wherein n is 1 to 10,
$R^5$ and $R^{5'}$ are independently selected from each other from the group consisting of H, substituted or unsubstituted $C_1$-$C_{10}$ alkyl, substituted or unsubstituted aryl or heteroaryl, substituted or unsubstituted $C_1$-$C_6$ alkyl-aryl and substituted or unsubstituted $C_1$-$C_6$-alkyl-heteroaryl.

6. A benzothiazole compound according to claim 5, wherein $R^1$ is H.

7. A benzothiazole compound according to claim 1, wherein $R^1$ is hydrogen, G is a pyrimidinyl group

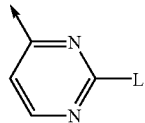

with L being either

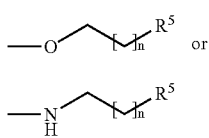

wherein n is 0, 1 or 2 and $R^5$ is an arylor heteroaryl.

8. A benzothiazole compound according to claim 7, wherein $R^5$ is phenyl, pyridyl, imidazolyl.

9. A benzothiazole compound according to claim 1 selected from the following group:

1,3-benzothiazol-2-yl(2-chloro-4-pyrimidinyl)acetonitrile;
1,3-benzothiazol-2-yl(2, 6-dimethoxy-4-pyrimidinyl)acetonitrile;
1,3-benzothiazol-2-yl(2-chloro-6-methyl-4-pyrimidinyl) acetonitrile;
1,3-benzothiazol-2-yl[2-(methylsulfanyl)-4-pyrimidinyl] acetonitrile;
1,3-benzothiazol-2-yl{6-chloro-5-nitro-4-pyrimidinyl}acetonitrile;
1,3-benzothiazol-2-yl(2-hydroxy-pyrimidinyl-4-yl) acetonitrile;
(2-chloropyrimidin-4-yl)[5-(trifluoromethyl)-1,3-benzothiazol-2-yl]acetonitrile;
(2E)-(2-chloro-4-pyrimidinyl)(3-methyl-1,3-benzothiazol-2(3H)-ylidene)ethanenitrile;
1,3-benzothiazol-2-yl(2-{[2-(1H-imidazol-5-yl)ethyl] amino}-4-pyrimidinyl)-acetonitrile;
1,3-benzothiazol-2-yl[2-(1-piperazinyl)-4 -pyrimidinyl] acetonitrile;
1,3-benzothiazol-2-yl[2-(4benzyl1piperidinyl)4 pyrimidinyl]acetonitrile;
1,3-benzothiazol-2-yl[2-(4-methyl-1-piperazinyl)-4-pyrimidinyl]acetonitrile;
1,3-benzothiazol-2-yl[2-(4morpholinyl)4 -pyrimidinyl] acetonitrile;
1,3-benzothiazol-2-yl[2-(methylamino)-4-pyrimidinyl] acetonitrile;
1,3-benzothiazol-2-yl(2-{4-[2-(4-morpholinyl)ethyl]-1-piperazinyl}-4-pyrimidinyl)acetonitrile;
1,3-benzothiazol-2-yl{2-[4-(benzyloxy)-1-piperidinyl]-4-pyrimidinyl}acetonitrile;
1,3-benzothiazol-2-yl[2-(4-hydroxy-1-piperidinyl)-4-pyrimidinyl]acetonitrile;
1,3-benzothiazol-2-yl(2hydrazino4 pyrimidinyl)acetonitrile;
1,3-benzothiazol-2-yl(2-{[2-(dimethylamino)ethyl] amino}-4-pyrimidinyl)acetonitrile;
1,3-benzothiazol-2-yl[2-(dimethylamino)-4-pyrimidinyl] acetonitrile;
1,3-benzothiazol-2-yl{2-[(2-methoxyethyl)amino]-4-pyrimidinyl}acetonitrile;
1,3-benzothiazol-2-yl{2-[(2-hydroxyethyl)amino]-4-pyrimidinyl}acetonitrile;
1,3-benzothiazol-2-yl[2-(propylamino)4 pyrimidinyl]acetonitrile;
1,3-benzothiazol-2-yl(2-{[3(1H-imidazol1yl)propyl] amino}4-pyrimidinyl)acetonitrile;
1,3-benzothiazol-2-yl[2-(1pyrrolidinyl)4 pyrimidinyl]acetonitrile;
1,3-benzothiazol-2-yl{2-[(2-phenylethyl)amino]-4-pyrimidinyl}acetonitrile;
1,3-benzothiazol-2-yl(2-{[2-(2pyridinyl)ethyl]amino}-4-pyrimidinyl)acetonitrile;
1,3-benzothiazol-2-yl{2-[(2-pyridinylmethyl)amino]-4-pyrimidinyl}acetonitrile;
1,3-benzothiazol-2-yl{2-[4(1H1, 2, 3benzotriazol1yl)-1-piperidinyl]-4-pyrimidinyl}acetonitrile;
1,3-benzothiazol-2-yl{2-[4(2pyrazinyl)1piperazinyl]-4-pyrimidinyl}acetonitrile;
1,3-benzothiazol-2-yl{2-[4(2pyrimidinyl)1piperazinyl]-4-pyrimidinyl}acetonitrile;
1,3-benzothiazol-2-yl(2-{[2-(3pyridinyl)ethyl]amino}-4-pyrimidinyl)acetonitrile;
1,3-benzothiazol-2-yl(5bromo2{[2-(dimethylamino) ethyl]amino}-4-pyrimidinyl)acetonitrile;
1,3-benzothiazol-2-yl{2-[(2morpholin-4-ylethyl)amino] pyrimidin-4-yl}acetonitrile;
1,3-benzothiazol-2-yl[2-(4{3(trifluoromethyl)sulfonyl] anhlino}piperidin-1-yl)pyrimidin-4-yl]acetonitrile;
1,3-benzothiazol-2-yl(2-{[3(2oxopyrrolidin-1-yl)propyl] amino }pyrimidin-4-yl)acetonitrile;
1,3-benzothiazol-2-yl(2-{methyl[3-(methylamino)propyl]amino }pyrimidin-4-yl)acetonitrile;
1,3-benzothiazol-2-yl(2-{[3-(4-methylpiperazin-1-yl) propyl]amino }pyrimidin-4-yl)acetonitrile;
1,3-benzothiazol-2-yl{2-[(3morpholin-4-ylpropyl)amino] pyrimidin-4-yl}acetonitrile;
1,3-benzothiazol-2-yl(2-{[2-(1methyl1Himidazol-4-yl) ethyl]amino }pyrimidin-4-yl)acetonitrile;
1,3-benzothiazol-2-yl(2-{[2-(1H-indol-3-yl)ethyl]amino }pyrimidin-4-yl)acetonitrile;
1,3-benzothiazol-2-yl(2-{[2-(4-hydroxyphenyl)ethyl] amino }pyrimidin-4-yl)acetonitrile;
tert-butyl({4-[1,3-benzothiazol-2-yl(cyano)methyl]pyrimidin-2-yl}amino)acetate
{2-[(3-aminopropyl)amino]pyrimidin-4-yl}(1,3-benzothiazol-2-yl)acetonitrile;
{2-[(2-aminoethyl)amino]pyrimidin-4-yl}(1,3-benzothiazol-2-yl)acetonitrile;
1,3-benzothiazol-2-yl(2-{[3-(dimethylamino)propyl] amino}pyrimidin-4-yl)acetonitrile;
1,3-benzothiazol-2-yl{2-[(2piperidin-1-ylethyl)amino] pyrimidin-4-yl}acetonitrile;
1,3-benzothiazol-2-yl(2-{[2-(1-methyl-1H-imidazol-5-yl)ethyl]amino }pyrimidin-4-yl)acetonitrile;
1,3-benzothiazol-2-yl[2-(benzylamino)pyrimidin-4-yl] acetonitrile;
isopropyl3({4[1,3-benzothiazol-2-yl(cyano)methyl]pyrimidin-2-yl}amino)propanoate
1,3-benzothiazol-2-yl{2-[(3-hydroxypropyl)amino]pyrimidin-4-yl}acetonitrile;
1,3-benzothiazol-2-yl{2-[(pyridin-3-ylmethyl)amino]pyrimidin-4-yl}acetonitrile;
(2-aminopyrimidin-4-yl)(1,3-benzothiazol-2-yl)acetonitrile;
1,3-benzothiazol-2-yl{2-[(pyridin-4-ylmethyl)amino]pyrimidin-4-yl}acetonitrile;

tert-butyl4-[2-({4-[1,3-benzothiazol-2-yl(cyano)methyl]pyrimidin-2-yl}amino)ethyl]phenylcarbamate (2-{[2-(4-aminophenyl)ethyl]amino}pyrimidin-4-yl)(1,3-benzothiazol-2-yl)acetonitrile;

1,3-benzothiazol-2-yl(2-{[2-(3,4-dimethoxyphenyl)ethyl]amino}pyrimidin-4-yl)acetonitrile;

1,3-benzothiazol-2-yl(2-{[2-(3-methoxyphenyl)ethyl]amino}pyrimidin-4-yl)acetonitrile;

1,3-benzothiazol-2-yl(2-{[2-(2-fluorophenyl)ethyl]amino}pyrimidin-4-yl)acetonitrile;

1,3-benzothiazol-2-yl[2-({2-[3-(trifluoromethyl)phenyl]ethyl}amino)pyrimidin-4-yl]acetonitrile;

1,3-benzothiazol-2-yl{2-[(2-hydroxy-2-phenylethyl)amino]pyrimidin-4-yl}acetonitrile;

1,3-benzothiazol-2-yl{2-[(2-{[3(trifluoromethyl)pyridin-2-yl]amino}ethyl)amino]pyrimidin-4-yl}acetonitrile;

1,3-benzothiazol-2-yl(2-{[2-(3-chlorophenyl)ethyl]amino}pyrimidin-4-yl)acetonitrile;

1,3-benzothiazol-2-yl(2-{[2-(3,4-dichlorophenyl)ethyl]amino}pyrimidin-4-yl)acetonitrile;

1,3-benzothiazol-2-yl(2-{[2-(4-methoxyphenyl)ethyl]amino}pyrimidin-4-yl)acetonitrile;

1,3-benzothiazol-2-yl(2-{[2-(4-methylphenyl)ethyl]amino}pyrimidin-4-yl)acetonitrile;

1,3-benzothiazol-2-yl(2-{[2-(3-fluorophenyl)ethyl]amino}pyrimidin-4-yl)acetonitrile;

1,3-benzothiazol-2-yl(2-{[2-(4-phenoxyphenyl)ethyl]amino}pyrimidin-4-yl)acetonitrile;

1,3-benzothiazol-2-yl(2-{[2-(2-phenoxyphenyl)ethyl]amino}pyrimidin-4-yl)acetonitrile;

1,3-benzothiazol-2-yl(2-{[2-(4-bromophenyl)ethyl]amino}pyrimidin-4-yl)acetonitrile;

1,3-benzothiazol-2-yl(2-{[2-(4-fluorophenyl)ethyl]amino}pyrimidin-4-yl)acetonitrile;

1,3-benzothiazol-2-yl{2-[(2-[1,1'biphenyl]-4-ylethyl)amino]pyrimidin-4-yl}acetonitrile;

1,3-benzothiazol-2-yl{2-[(2-{4-[hydroxy(oxido)amino]phenyl}ethyl)amino]pyrimidin-4-yl}acetonitrile;

1,3-benzothiazol-2-yl(2-{[2-(1H1,2,4triazol-1-yl)ethyl]amino}pyrimidin-4-yl)acetonitrile;

1,3-benzothiazol-2-yl(2-{[3(1H-pyrazol-1-yl)propyl]amino}pyrimidin-4-yl)acetonitrile; 4-[2-({4-[1,3-benzothiazol-2-yl(cyano)methyl]pyrimidin-2-yl}amino)ethyl]benzenesulfonamide {2-[(2-pyridin-3-ylethyl)amino]pyrimidin-4-yl}[5-(trifluoromethyl)-1,3-benzothiazol-2-yl]acetonitrile;

1,3-benzothiazol-2-yl{2-[(1H-tetraazol-5-ylmethyl)amino]pyrimidin-4-yl}acetonitrile;

1,3-benzothiazol-2-yl[2-(benzyloxy)pyrimidin-4-yl]acetonitrile;

1,3-benzothiazol-2-yl{2-[(4pyridin-3-ylbenzyl)oxy]pyrimidin-4-yl}acetonitrile;

1,3-benzothiazol-2-yl[2-(pyridin-4-ylmethoxy)pyrimidin-4-yl]acetonitrile;

1,3-benzothiazol-2-yl[2-(pyridin-2-ylmethoxy)pyrimidin-4-yl]acetonitrile;

1,3-benzothiazol-2-yl[2-(3-pyridin-2-ylpropoxy)pyrimidin-4-yl]acetonitrile;

1,3-benzothiazol-2-yl{2-[(4-methoxybenzyl)oxy]pyrimidin-4-yl}acetonitrile;

1,3-benzothiazol-2-yl[2-(pyridin-3-ylmethoxy)pyrimidin-4-yl]acetonitrile;

1,3-benzothiazol-2-yl{2-[2-(4-methoxyphenyl)ethoxy]pyrimidin-4-yl}acetonitrile;

1,3-benzothiazol-2-yl[2-([1,1'biphenyl]-3-ylmethoxy)pyrimidin-4-yl]acetonitrile;

1,3-benzothiazol-2-yl{2-[(3,4,5-trimethoxybenzyl)oxy]pyrimidin-4-yl}acetonitrile;

1,3-benzothiazol-2-yl{2-[(3,4-dichlorobenzyl)oxy]pyrimidin-4-yl}acetonitrile;

1,3-benzothiazol-2-yl[2-({3[-(dimethylamino)methyl]benzyl}oxy)pyrimidin-4-yl]acetonitrile;

1,3-benzothiazol-2-yl{2-[(1oxidopyridin-3-yl)methoxy]pyrimidin-4-yl}acetonitrile;

1,3-benzothiazol-2-yl(2-{[4(morpholin-4-ylmethyl)benzyl]oxy}pyrimidin-4-yl)acetonitrile;

1,3-benzothiazol-2-yl{2-[(4pyridin-2-ylbenzyl)oxy]pyrimidin-4-yl}acetonitrile;

1,3-benzothiazol-2-yl(2-{[4(piperidin-1-ylmethyl)benzyl]oxy}pyrimidin-4-yl)acetonitrile;

1,3-benzothiazol-2-yl[2-(4-methoxyphenoxy)pyrimidin-4-yl]acetonitrile;

1,3-benzothiazol-2-yl[2-(4-butoxyphenoxy)pyrimidin-4-yl]acetonitrile;

{2-[4-(4-acetylpiperazin-1-yl)phenoxy]pyrimidin-4-yl}(1,3-benzothiazol-2-yl)acetonitrile;

[2-(4-methoxyphenoxy)pyrimidin-4-yl][5-(trifluoromethyl)-1,3-benzothiazol-2-yl]acetonitrile;

1,3-benzothiazol-2-yl(pyrimidin-4-yl)acetonitrile; and

N-[2-({4-[1,3-benzothiazol-2-yl(cyano)methyl]pyrimidin-2-yl}amino)ethyl]-4-chlorobenzamidel, 3-benzothiazol-2-yl(2-methoxy-4-pyrimidin-yl)acetonitrile.

10. A -benzothiazol-e compound according to claim 9, selected from the group consisting of:

1,3-benzothiazol-2-yl(2-chloro-4-pyrimidin-yl)acetonitrile;

1,3-benzothiazol-2-yl[2-(methylsulfanyl)-4-pyrimidin-yl]acetonitrile;

1,3-benzothiazol-2-yl(2-{[2-(1H-imidazol5yl)ethyl]amino}-4-pyrimidin-yl)acetonitrile; 1,3-benzothiazol-2-yl[2-(methylamino)-4-pyrimidin-yl]acetonitrile;

1,3-benzothiazol-2-yl{2-[(2-hydroxyethyl)amino]-4-pyrimidin-yl}acetonitrile; 1,3-benzothiazol-2-yl[2-(benzyloxy)pyrimidin-4-yl]acetonitrile;

1,3-benzothiazol-2-yl[2-(4-methoxyphenoxy)pyrimidin-4-yl]acetonitrile;

1,3-benzothiazol-2-yl(2-methoxy-4-pyrimidinyl)acetonitrile; and 1,3-benzothiazol-2-yl(2-{[2-(3pyridinyl)ethyl]amino}-4-pyrimidinyl)acetonitrile.

11. A benzothiazole compound according to claim 1, which is 1,3-benzothiazol-2-yl([2-{[4-(morpholin-4-ylmethyl)benzyl]oxy}-pyrimidin-4-yl)acetonitrile.

12. A benzothiazole compound according to claim 5, wherein n is 1to 6.

13. Process for the preparation of a benzothiazole compound according to claim 1, wherein the following reaction is performed:

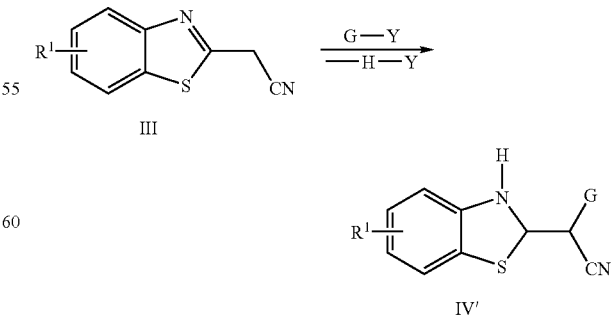

whereby G is as described above and Y is a suitable leaving group like halogen.

14. Process according to claim 13, wherein the following reactions are performed:
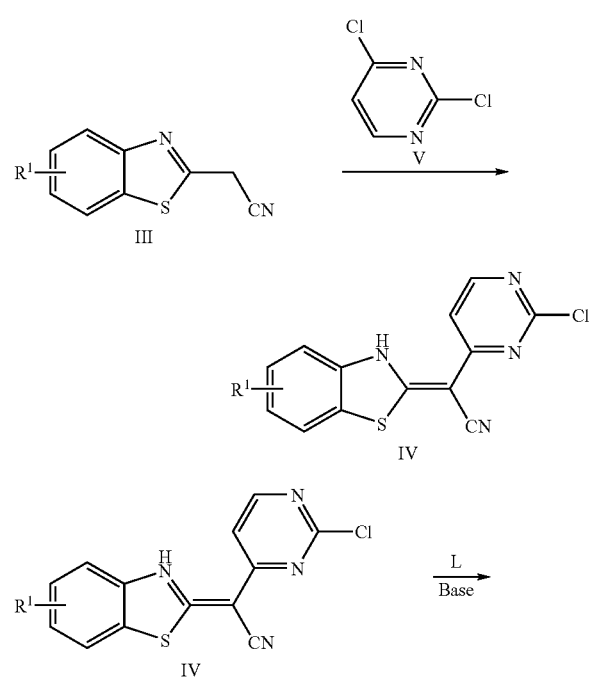
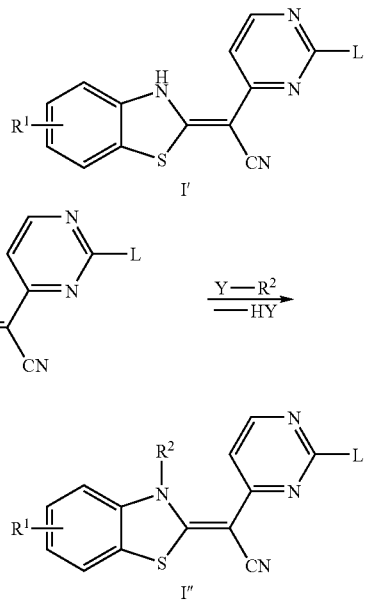
with $R^1$, $R^2$, Y and L being as described above.
15. A pharmaceutical composition containing at least one benzothiazole compound according to claim 1 and a pharmaceutically acceptable carrier, diluent or excipient thereof.
* * * * *